United States Patent
Marien et al.

(10) Patent No.: US 12,121,272 B2
(45) Date of Patent: Oct. 22, 2024

(54) TWO-PART SURGICAL GUIDE

(71) Applicant: MATERIALISE N.V., Leuven (BE)

(72) Inventors: Rosalien Marien, Leuven (BE); Toon Lenaerts, Leuven (BE); Frederik Verstreken, Schoten (BE); Wilfried Vancraen, Huldenberg (BE); Bram Lenaerts, Pulle (BE)

(73) Assignee: MATERIALISE N.V., Leuven (BE)

( * ) Notice: Subject to any disclaimer, the term of this patent is extended or adjusted under 35 U.S.C. 154(b) by 665 days.

(21) Appl. No.: 17/348,222

(22) Filed: Jun. 15, 2021

(65) Prior Publication Data

US 2021/0307796 A1 Oct. 7, 2021

Related U.S. Application Data

(63) Continuation-in-part of application No. 15/993,985, filed on May 31, 2018, now Pat. No. 11,123,115, and
(Continued)

(51) Int. Cl.
*A61B 17/80* (2006.01)
*A61B 17/15* (2006.01)
(Continued)

(52) U.S. Cl.
CPC ............ *A61B 17/80* (2013.01); *A61B 17/151* (2013.01); *A61B 17/809* (2013.01); *G16H 50/50* (2018.01);
(Continued)

(58) Field of Classification Search
CPC .................. A61B 17/80; A61B 17/809; A61B 2017/00526
See application file for complete search history.

(56) References Cited

U.S. PATENT DOCUMENTS

| 4,421,112 A | 12/1983 | Mains et al. |
| 2003/0040748 A1 | 2/2003 | Aikins et al. |

(Continued)

FOREIGN PATENT DOCUMENTS

| AU | 2014262239 A1 | 12/2014 |
| JP | 858209343 A | 12/1983 |

(Continued)

*Primary Examiner* — Sameh R Boles
(74) *Attorney, Agent, or Firm* — Dinsmore & Shohl LLP

(57) ABSTRACT

Certain aspects relate to a two-part surgical guide system for use in surgical procedures such as osteotomies. Certain aspects provide a first part including a contact surface configured to conform to a portion of an anatomy of the patient to substantially restrict movement of the first part with respect to the anatomy of the patient. The first part further includes guiding elements configured to receive reference pins and guide placement of the reference pins in the anatomy of the patient. Certain aspects further provide a second part, separate from the first part. The second part includes apertures. Each aperture is configured to receive a reference pin and substantially restrict movement of the second part with respect to the anatomy of the patient. The second part further includes a functional element for guiding a procedure on the anatomy of the patient.

19 Claims, 13 Drawing Sheets

Related U.S. Application Data a continuation-in-part of application No. 15/768,793, filed as application No. PCT/US2016/057867 on Oct. 20, 2016, now abandoned, said application No. 15/993,985 is a continuation of application No. 14/518,647, filed on Oct. 20, 2014, now abandoned, which is a continuation of application No. PCT/EP2013/058041, filed on Apr. 18, 2013.

(60) Provisional application No. 62/245,255, filed on Oct. 22, 2015, provisional application No. 61/625,819, filed on Apr. 18, 2012.

(51) Int. Cl.
*G16H 50/50* (2018.01)
*G16Z 99/00* (2019.01)
*A61B 17/00* (2006.01)
*A61B 34/10* (2016.01)

(52) U.S. Cl.
CPC .... *G16Z 99/00* (2019.02); *A61B 2017/00526* (2013.01); *A61B 2034/102* (2016.02); *A61B 2034/108* (2016.02)

(56) References Cited

U.S. PATENT DOCUMENTS

| | | |
|---|---|---|
| 2009/0088763 A1 | 4/2009 | Aram et al. |
| 2011/0015636 A1 | 1/2011 | Katrana et al. |
| 2011/0172672 A1* | 7/2011 | Dubeau ............ A61B 17/151 606/87 |
| 2014/0276867 A1 | 9/2014 | Kelley et al. |
| 2015/0051650 A1* | 2/2015 | Verstreken ............ G16Z 99/00 606/281 |
| 2015/0223852 A1 | 8/2015 | Lietz et al. |

FOREIGN PATENT DOCUMENTS

| | | |
|---|---|---|
| JP | 2010540123 A | 12/2010 |
| JP | 2013521046 A | 6/2013 |

* cited by examiner

TWO-PART SURGICAL GUIDE

CROSS-REFERENCE TO RELATED APPLICATIONS

This application is a continuation-in-part of U.S. application Ser. No. 15/768,793, filed Apr. 16, 2018, which is a national stage entry of International Application No. PCT/US2016/057867, filed Oct. 20, 2016, which claims priority to U.S. Provisional Application No. 62/245,255, filed Oct. 22, 2015. The contents of each of these applications are incorporated by reference in their entirety. This application is also a continuation-in-part of U.S. application Ser. No. 15/993,985, filed May 31, 2018, which is a continuation of U.S. application Ser. No. 14/518,647, filed Oct. 20, 2014, which is a continuation of International Application No. PCT/EP2013/058041, filed Apr. 18, 2013, which claims priority to U.S. Provisional Application No. 61/625,819, filed Apr. 18, 2012. The entire contents of each of the above-referenced patent applications are hereby incorporated by reference.

BACKGROUND OF THE INVENTION

Field of the Invention

This application relates to surgical guides. More particularly, this application relates to a two-part surgical guide system for use in surgical procedures such as osteotomies, for example.

Description of the Related Technology

Performing surgical procedures, such as osteotomies (e.g. high-tibia osteotomy (HTO), femoral osteotomies, innominate osteotomies, other tibial osteotomies, etc.) can be a challenging surgical procedure. For example, in an osteotomy, a bone is cut to either shorten, lengthen or realign at least a portion of the bone, such as to change an alignment angle of the bone. In an osteotomy, accurate positioning of the cut in the bone, as well as fixation of the bone fragments in the accurate changed position is important to ensure a successful surgery.

Traditionally, these types of surgeries are planned using X-ray images of the surgical site to determine how best to carry out the procedure. X-ray imaging, however, gives a limited view of the actual three-dimensional ("3-D") anatomy of the patient and on the 3-D correction to be made to the anatomy of the patient (e.g. cut and change in position of the bone of the patient). These limitations in X-ray technology result in the need for extensive checking of various parameters (e.g. cut positions, bone positions, drill positions, alignments, etc.) during surgical procedures. Often, the checking process involves extensive fluoroscopy, which results in a more time-consuming and complicated procedure.

Accordingly, more precise imaging technologies have emerged as improvements for the planning of surgical procedures, such as osteotomies. These more precise imaging technologies, such as computerized tomography (CT) scanning, magnetic resonance imaging (MRI), and the like, allow for precise measurements of the surgical site to be taken prior to the procedure. Accordingly, planned operations, such as planned cuts, drilling or bone fragment repositioning can be precisely mapped out in advance.

In some cases, patient-specific devices such as patient-specific surgical guides are designed and manufactured based on imaging of the surgical site. However, current patient-specific guides, such as those utilized in osteotomies, have certain drawbacks. For example, these patient-specific guides can be quite bulky, and therefore require larger incisions to be made to utilize the patient-specific guide during the surgical procedure to accommodate the bulky patient-specific guide. For example, large portions of soft-tissue of the patient may need to be cut or moved to accommodate the bulky patient-specific guide. In particular, the current patient-specific guides may need to be designed to interact with enough portions of the bone of the patient to stay in place during surgery, and include all the necessary functional elements (e.g. drill guides, cutting guides, etc.) for guiding the surgeon to ensure the planned operations to the bone are made in the right positions. Further, the current bulky patient-specific guides can make the surgical procedure more challenging and less precise, because the surgical site becomes too crowded. Accordingly, improved patient-specific surgical guides, such as patient-specific osteotomy guides, and techniques for using those patient-specific surgical guides are needed which do not suffer from the drawbacks present in current devices.

SUMMARY

Certain embodiments of this disclosure provide a patient-specific system for performing an osteotomy on a bone of a patient, the system comprising: a first part comprising: at least one contact surface configured to conform to at least one portion of the bone such that when the at least one contact surface is positioned on the at least one portion of the bone, movement of the first part is substantially restricted with respect to the bone; and a plurality of guiding elements configured to guide placement of a plurality of reference pins in the bone; and a second part, separate from the first part, the second part comprising: a plurality of apertures each with a shape corresponding to a reference pin, each of the plurality of apertures being configured to receive one of the plurality of reference pins and substantially restrict movement of the second part with respect to the bone when the plurality of reference pins are received; and at least one functional element for drilling a hole in the bone.

Certain embodiments of this disclosure provide a method for performing an osteotomy on a bone of a patient, the method comprising: placing a first part of a two-part osteotomy guide within a surgical site of the bone of the patient, the first part comprising: at least one contact surface configured to conform to at least one portion of the bone such that when the at least one contact surface is positioned on the at least one portion of the bone, movement of the first part is substantially restricted with respect to the bone; and a plurality of guiding elements configured to guide placement of the reference pins in the bone; positioning the first part on the bone by aligning the at least one contact surface with the at least one portion of the bone to secure the first part to the bone; guiding placement of the reference pins into the bone based on the plurality of guiding elements; removing the first part from the bone; positioning a second part of the two-part osteotomy guide on the bone by receiving the reference pins in a plurality of apertures of the second part, the second part comprising: the plurality of apertures each with a shape corresponding to a reference pin, each of the plurality of apertures being configured to receive one of the plurality of reference pins and substantially restrict movement of the second part with respect to the bone when the plurality of reference pins are received; and at least one functional element for guiding a procedure on the bone;

drilling at least one additional hole into the bone through the at least one functional element; removing the second part from the bone; performing an osteotomy cut to the bone; and securing an osteosynthesis implant to the bone using the at least one drilled hole.

Certain embodiments of this disclosure provide a patient-specific system for performing an surgery on a patient, the system comprising: a first part comprising: at least one contact surface configured to conform to at least one portion of an anatomy of the patient such that when the at least one contact surface is positioned on the at least one portion of the anatomy of the patient, movement of the first part is substantially restricted with respect to the anatomy of the patient; and a plurality of guiding elements configured to receive a plurality of reference pins and guide placement of the reference pins in the anatomy of the patient; and a second part, separate from the first part, the second part comprising: a plurality of apertures each with a shape corresponding to a reference pin, each of the plurality of apertures being configured to receive one of the plurality of reference pins and substantially restrict movement of the second part with respect to the anatomy of the patient when the plurality of reference pins are received; and at least one functional element for guiding a procedure on the anatomy of the patient.

Provided herein are orthopedic devices which allow fixation of two or more partially or entirely disconnected bone fragments according to a pre-operatively determined position relative to each other and methods for placing such orthopedic devices.

More particularly, disclosed herein is a bone plate for use in orthopedic surgery for fixating two or more bone fragments according to a pre-operative plan, comprising: a rigid structure comprising one or more patient-specific features allowing the positioning of the bone plate onto at least one bone fragment in a specific position which position is determined based on pre-operative planning; fixation features for fixing the bone plate onto the bone or bone fragments; and positioning elements which aid the positioning of the bone plate onto the bone.

More particularly, said bone plate is a bone plate for fixing two bone fragments to each other, wherein the bone plate comprises at least two patient-specific features, each corresponding to or matching a feature on one of the bone fragments which are to be fixed together. More particularly, the patient-specific features are selected such that in the pre-operatively determined correct relative position of the bone fragments, the patient-specific features on the bone plate optimally match the corresponding features on the bone fragments.

More particularly, said bone plate provided is a bone plate wherein the rigid structure which is the supporting element may vary in thickness. In further particular embodiments, the rigid structure of the bone plate is locally increased around the osteotomy or fracture plane of the bone fragments.

In particular embodiments, bone plates are provided wherein the positioning elements are non-threaded structures extending from the rigid structure of the bone plate, such as, but not limited to pins, pegs or hooks. Additionally or alternatively, the positioning elements may be structures holes for positioning devices such as are non-threaded pin-, peg- or hook-like structures. Optionally, the positioning elements may be detachable from the bone plate rigid structure.

In particular embodiments, the fixation elements are threaded holes for screws.

The position and orientation of the positioning elements and fixation features are determined according to a pre-operative plan.

The application further provides guides for drilling holes into bone fragments corresponding to the desired position of the screws which are introduced in the fixation features of a bone plate for fixing said bone fragments. More particularly, the application envisages combinations of a bone plate for fixing onto two bone fragments or a defect bone area as described herein comprising a rigid structure, one or more patient-specific features and fixation features and a guide for drilling holes into the bone or bone fragments in pre-operatively planned position of the fixation elements.

In particular embodiments, bone plates are provided which comprise two or more separate parts, each comprising a rigid structure with one or more fixation features and optionally one or more positioning elements, which can be combined and attached to each other to form a one-piece bone plate after placement on the bone fragments and positioning the bone fragments in the pre-operatively planned position.

In a further particular embodiment, methods are provided for generating bone plates providing a tailored and defect-specific approach comprising the steps of: generating a 2-dimensional (2D) or 3-dimensional (3D) model of the bone defect or envisaged osteotomy based on one or more images of the bone and the surgical plan; designing, based on said 2D or 3D model, a model corresponding to the envisioned repair of said bone defect/envisaged result of the osteotomy; generating a bone plate with a rigid structure based on the information above comprising: one or more patient-specific features matching or corresponding to the surface of a bone fragment in the area close to the defect, and one or more fixation features whereby the position and orientation is selected based on the information above so as to be suitable for fixing the bone plate to said bone fragments.

More particularly, methods are provided for generating a guide for a bone plate as described herein, the method comprising, determining, based on the pre-operative plan the desired positions of the holes for the fixation of the bone plate to the bone fragments, and generating a guide comprising drill-guides for drilling holes in to the bone or bone fragments to receive the fixation elements (such as screws) introduced through the fixation features of the bone plate. More particularly the methods for generating the bone plate (and optionally the guide) involve performing virtual surgery on the defective bone to identify the defect site and determining the shape and/or form parameters of the defect or of the structure necessary to fix the defect.

In a further particular embodiment, a method is provided for fixating bone fragments according to a predetermined position comprising the steps of: drilling holes into the bone or bone fragments, for receiving the fixation elements; repositioning the bone fragments into the correct position for healing, positioning a bone plate as disclosed herein on the bone fragments using the positioning elements; and introducing fixation elements into the fixation features on the bone plate, thereby fixing the bone fragments or bone according to a predetermined position.

More particularly, the method comprises first a step of positioning a bone plate as disclosed herein on one of the bone fragments, followed by repositioning the bone fragments into the correct position for healing using the bone plate fixed onto one of the bone fragments as a hinge and further positioning the bone plate onto the bone fragments.

The application further claims kits comprising tools for performing at least part of the surgical procedures described herein. In particular embodiments the kits comprise: a patient specific bone plate as disclosed herein; and a guide for drilling holes corresponding to the desired location and direction of the fixation elements, which are to be introduced through the fixation features of the bone plate.

More particularly, the kits may further comprise positioning devices which fit into a positioning feature of the bone plate and/or fixation elements corresponding to the fixation features on the bone plate for further fixing the bone plate into the correct position on the bone fragments.

BRIEF DESCRIPTION OF THE DRAWINGS

The following references are used throughout FIGS. 9-12: bone (1), bone plate (2), bone plate supporting structure (3), bone plate positioning elements (4), bone plate fixation features (5), fixation elements (6), patient-specific features (7), drill guide (10), K-wire (11), hole (12), cutting guide (13) and bone osteotomy (14).

DETAILED DESCRIPTION OF CERTAIN INVENTIVE EMBODIMENTS

Figure 1A:
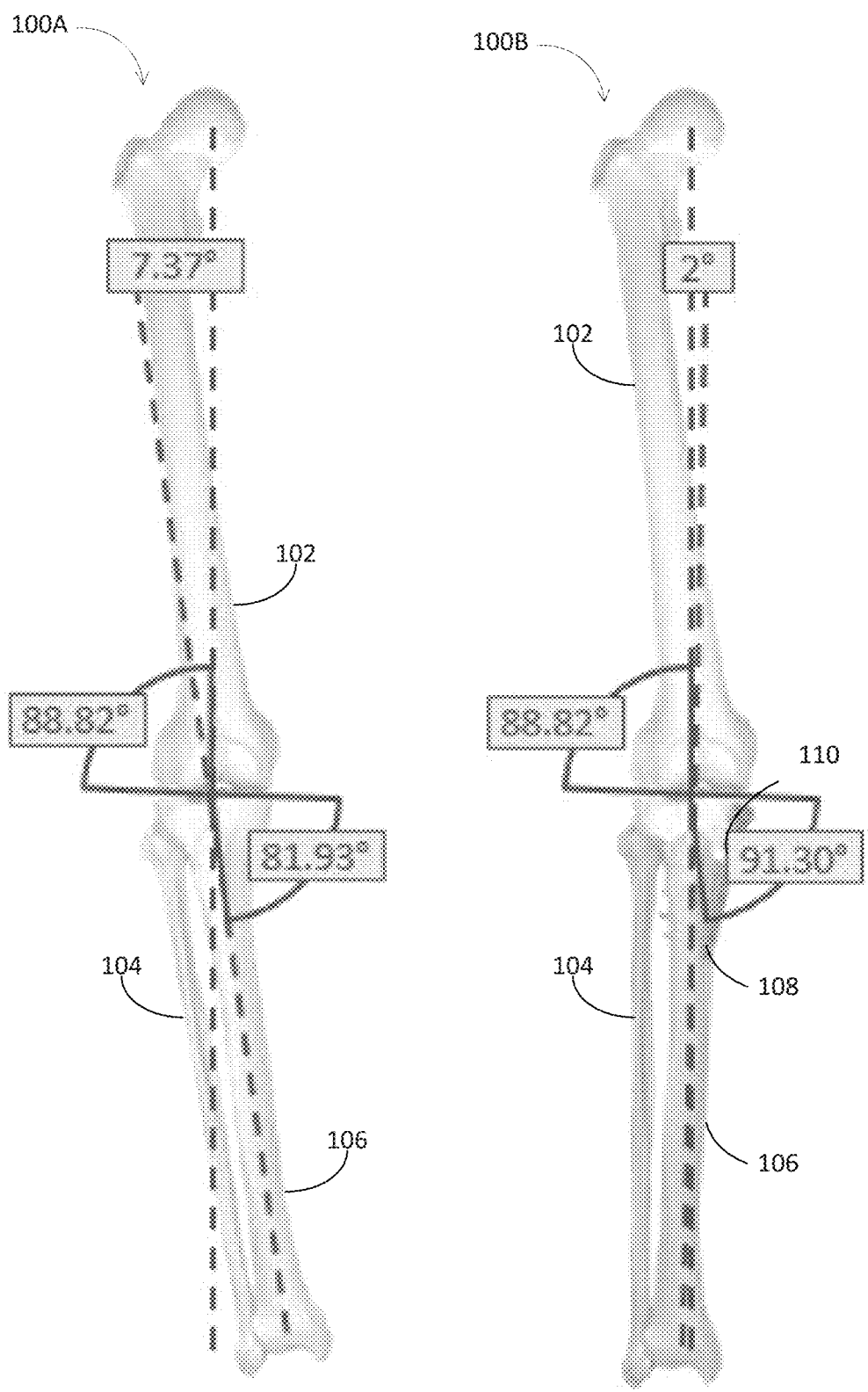
FIG. 1A illustrates 3-D models of a bone of a patient that is to undergo surgery, in accordance with certain embodiments.

The following description and the accompanying figures are directed to certain specific embodiments. The embodiments described in any particular context are not intended to limit this disclosure to the specified embodiment or to any particular usage. Those of skill in the art will recognize that the disclosed embodiments, aspects, and/or features are not limited to any particular embodiments. In certain embodiments and aspects described herein, a surgical procedure can be an osteotomy, an ostectomy, an arthrodesis, an arthroplasty, a chondroplasty, a fracture repair, etc. In certain embodiments and aspects described herein, a bone anatomy can be a tibia, a femur, a fibula, a radius, an ulna, a humerus, a tarsal, a metatarsal, a carpal, a metacarpal, a clavicle, a scapula, a pelvis, a knee joint, an elbow joint, a shoulder joint, a hip joint, an ankle, a vertebra, a spine, etc.

Embodiments of the inventions described herein relate to the design, manufacture, and use of a set of two guides for performing a surgical procedure on a patient. Certain embodiments more specifically relate to the design, manufacture, and use of a set of two guides for performing an osteotomy on a patient. In some embodiments, the two-part surgical guides described herein may be manufactured using additive manufacturing techniques to make the guides patient-specific.

As used herein, the term "patient-specific" relates to any surgical, therapeutic or diagnostic device or tool such as an implant, a prosthesis or a surgical guide which is designed based on an individual patient's anatomy to include features which have a custom fit and/or to perform a customized function for a specific patient. The use of guides and implants which are patient-specific makes it possible to ensure an improved or optimized accuracy of the surgical intervention and an improved anatomical fit for prosthetic structures thereby ensuring optimized functionality for each patient. Even when such devices are used in combination with standard implants, tools, devices, surgical procedures, or other methods, important benefits in accuracy of placement can be obtained.

These two-part surgical guides overcome several of the drawbacks present in current patient-specific guide technologies by decoupling the registration (e.g. fitting) surface of the patient-specific guide from most of the functional elements (e.g. drilling guides, cutting guides, etc.) provided to assist the surgeon. By decoupling the registration surface from the functional elements, the size of each of the individual guide parts can be kept small, which may reduce the size of incision needed for performing a surgical procedure, thereby reducing complications such as healing time and scarring from the surgical procedure . . . .

In some embodiments, the registration surface may refer to one or more contact surfaces on the surgical guide that correspond to and conform to portions (e.g. surfaces) on the patient's anatomy (e.g. bone), such that when the surgical guide is positioned on the patient's anatomy with the registration surfaces contacting the surfaces of the patient's anatomy, the surgical guide is restricted from movement with respect to the patient's anatomy and is accurately positioned on the patient's anatomy. For example, in some embodiments, the registration surface may be designed so as to substantially conform to only a single position on the patient's anatomy.

Not all surfaces on the patient's anatomy may provide the necessary fit and stability when interacting with the surgical guide to ensure the proper positioning of the surgical guide. For example, certain portions of the patient's anatomy may include relatively smooth cylindrical surfaces such that merely having the surgical guide conform to and contact such a smooth surface may not ensure proper positioning of the surgical guide as the surgical guide may easily move. Accordingly, the registration surface may need to be configured to contact the patient's anatomy at multiple surfaces, such as surfaces with more specific features that allow the surgical guide to substantially conform to only a single position on the patient's anatomy. For example, in a high tibia osteotomy ("HTO") procedure, suitable surfaces on the patient's anatomy may include one or more of an anterior surface around the tibial tuberosity, a surface proximal from the attachment of the patellar tendon, and a surface distal from the attachment of the patellar tendon. These multiple surfaces on the patient's anatomy may be on opposite sides of a bone, or at a distance from one another, such that it may significantly increase the bulk of a single-piece patient-specific guide. In particular, a single piece patient-specific guide, as discussed, may then need to both include the functional elements that add bulk, and the registration surfaces that add bulk. Due to this bulky design, it may be difficult to actually position the surgical guide on the patient's anatomy, since the bulky design makes it difficult to maneuver the surgical guide on the patient's anatomy due to other soft tissues at the surgical site. Therefore, the single-piece patient-specific guides may require larger cuts in the soft tissue at the surgical site to position the surgical guide as compared to the embodiments presented herein.

For example, in some embodiments, for a two-part surgical guide, a profile of the guide part with the registration surface may be designed to have a low profile (e.g. reduced dimensions, such as thickness) so the guide part can be placed on the patient's anatomy with minimal disruption to soft tissue near the surgical site. For example, in some embodiments, the guide part (also referred to herein as the first part) may have a profile between 1 to 3 mm. In particular, the low profile of the guide part may allow portions of the guide part to be positioned between the soft tissue and the bone of the patient that the guide part attaches to, therefore avoiding the need to damage or cut the soft tissue. In some embodiments, the guide part may further have tapered (e.g. rounded or chamfered) edges to facilitate the positioning of the guide part between the soft tissue and the bone. The low profile of the guide part may further help facilitate with removal of the guide part from the patient's anatomy by providing flexibility to the guide part to assist in removal. In contrast, current bulky patient-specific guides are too thick to be flexible, and therefore may require additional features such as additional apertures or additional surgical steps such as removal and reinsertion of pins to ensure the guide part can be removed from the patient's anatomy. Such additional features may add cost or reduce effectiveness of the guide as the additional apertures may allow for more movement of surgical tools during surgical procedures. Such additional surgical steps increase surgery time and introduce potential sources of error.

In certain embodiments, a first part of the two-part guide may be designed specifically with fitting stability as its main purpose. As such, the first part of the two-part guide may be designed without many of the functional elements that are typically present on surgical guides, such as osteotomy guides. Further, the first part includes a registration surface to stably fit onto the patient's anatomy. In some embodiments, the first part of the two-part guide may include one, two or more guiding elements (e.g. drill guides) for receiving reference pins (e.g. guide wires). For example, the two-part guide may include two or more drill guides (e.g. drill cylinders) for drilling holes into an anatomy of the patient (e.g. bone) and inserting guide wires, such as k-wires, inside of the holes and into the patient's anatomy. In some embodiments, reference pins may be directly drilled into the bone through the drill guides. In some embodiments, the guide wires are left in the bone when the first part of the two-part guide is removed. As discussed, in some embodiments, the first part of the two-part guide has a flexible design due to it having a low profile/reduced thickness at least in certain portions, to facilitate removal of the first part even with the guide wires inserted in the bone and interacting with the drill cylinders. Further, the low profile of the first part may facilitate positioning the first part on the bone, with reduced damage to soft tissues surrounding the bone.

In some embodiments, the guide wires may be used in performing an osteotomy. In particular, the guide wires may be used for sliding the sawblade against the guide wires to guide the sawblade when performing the osteotomy cut.

A second part of the two-part guide is also provided. The second part of the two-part guide is configured to reference its position on the patient's anatomy based on the guide wires inserted in the patient's anatomy using the first part. By referencing its position based on the inserted guide wires, the need for a large fitting surface is eliminated. In particular, the second part may include apertures (e.g. holes, cylindrical openings, etc.) configured to receive the guide wires and therefore position the second part with respect to the patient's anatomy in a particular position. In particular, in certain aspects the apertures may be sized and shaped to correspond to the guide wires to restrict movement of the second part when the guide wires are inserted. The second part may further include one or more contact surfaces that conform to one or more portions of the underlying anatomy of the patient when positioned on the guide wires and the anatomy of the patient. These contact surfaces may provide additional stability (e.g. prevent wobble) of the second part, but are not sufficient alone (e.g. without the guide wires) to securely position the second part on the patient's anatomy.

Accordingly, the bulk and size required for the second part is reduced, and the second part may only need to conform to a smaller area on the patient's anatomy, thereby reducing the incision required for the surgical site. Further, even if the second part includes some additional bulk (e.g. thickness) to accommodate the functional features (e.g. cut guiding surfaces, drill guides, reamer guides, etc.) used for guiding a procedure (e.g. drilling, cutting, reaming, etc.) on the patient's anatomy as compared to the first portion, the second part does not need to conform to all the surfaces on the patient's anatomy that the first part does. Therefore the extra bulk of the second part may be limited to a smaller area corresponding to a smaller incision at the surgical site. For example, the second part may be designed to not extend beyond the apertures and functional elements of the second part in a direction substantially parallel to a surface of the patient's anatomy by more than, for example, 3 mm, 2 mm, or 1 mm, since the additional extension is not needed for stability, thereby reducing bulk and a footprint of the second part.

Moreover, in some embodiments, the second part of the two-part guide does not include a cut guiding surface (e.g. a cut slot, a sawblade-guiding surface, etc.) for guiding cuts into the bone, as the guide wires left in place after the removal of the first part serve that purpose. Accordingly, the bulk of the second part can be further reduced. In some embodiments, the second part of the two-part guide may still include at least one cut-guiding surface, however, to assist in the surgical procedure, while still providing reduced bulk as compared to current patient-specific surgical guides. For example, if the two-part guide is designed for a closing wedge osteotomy where a portion (e.g. wedge) of the bone is removed, two cuts in the bone may be used, and therefore the second part may include one or more cut-guiding surfaces to guide one or more of the multiple cuts.

In some embodiments, instead of adding bulk and including multiple cut-guiding surfaces for procedures utilizing multiple cuts, the first part of the two-part guide may include multiple drilling guides positioned on the first part such that when the first part is positioned on the bone, the drilling guides align with positions where the multiple cuts are performed. For example, two or more drilling guides may be aligned at each cut position. The drilling guides may be used to guide drilling into the bone and insertion of guide wires into the bone. The first part may then be removed, and the cuts performed using the guide wires to guide the cuts as discussed herein.

As described, the second part may include one or more functional elements of a suitable type depending on the procedure to be performed. In some embodiments, the functional elements may comprise a radiopaque material that can be seen on a fluoroscopy (real-time use of an imaging technique such as X-rays) and used to check on the status of the surgery in real time.

Certain embodiments described herein are described with respect to osteotomies and accordingly, two-part guides for osteotomies. Accordingly, certain described aspects may pertain specifically to osteotomies and provide certain benefits over current guides and techniques for performing osteotomies, such as the configuration of functional elements on the guides specifically for performing osteotomies. However, certain described aspects may also be used for two-part guides for other surgical procedures, as would be apparent to one of skill in the art. Accordingly, certain embodiments herein may relate to two-part guides for surgical procedures other than osteotomies as well as osteotomies.

FIG. 1A illustrates 3-D models of a bone of a patient that is to undergo surgery, in accordance with certain embodiments. In this particular example, the surgical procedure to be performed is an osteotomy for a proximal tibia. In particular, FIG. 1A illustrates a pre-surgery bone anatomy 100A and a desired bone anatomy 100B that the surgery is trying to achieve. The 3-D models may be used as part of a preplanning of the surgical procedure using virtual 3-D technology. In this particular example, the 3-D reconstruction plan including virtual 3-D models of the pre-surgery bone anatomy 100A and the desired bone anatomy 100B is generated by a computing device based on CT data acquired using a suitable scan program and a suitable CT scanner. However, as discussed herein, a 3-D model may be generated using other appropriate imaging techniques (e.g. MRI, X-rays, etc.)

As shown, the 3-D models include images of various bones in the leg of the patient. The pre-surgery bone anatomy 100A includes the femur 102. At the distal end of the femur 102 is the knee joint, which joins the femur to the fibula 104 and the tibia 106. The mechanical axes and angles of the pre-surgery bone anatomy 100A are computed and may be displayed on a computer monitor for evaluation by a surgeon and/or a clinical engineer.

Figure 1B:
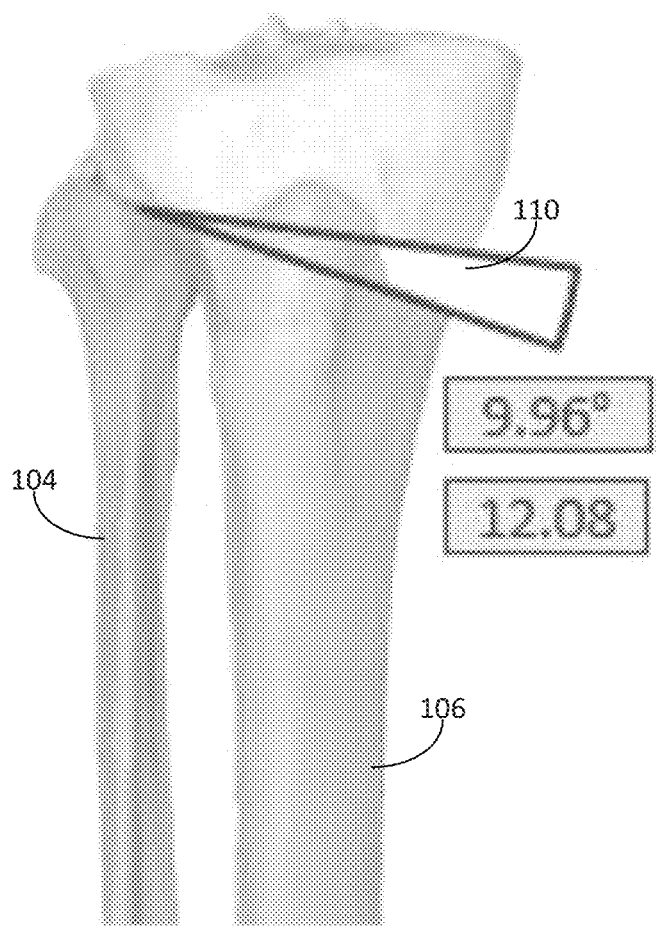
FIG. 1B is a close-in view of the planned osteotomy cut shown in FIG. 1A, in accordance with certain embodiments.

The desired bone anatomy 100B shows how the angle of the tibia with respect to the femur will change after completion of the osteotomy procedure. Using the scanned CT data, a desired angle of correction may be determined for the bone anatomy, and the mechanical axes upon which the bone will be cut and realigned may be defined as shown. In this example, the desired bone anatomy 100B is achieved by removing a wedge 110 out of the proximal tibia and supporting the modified bone using an osteosynthesis plate 108. FIG. 1B illustrates a close-in view of the planned osteotomy cut shown in FIG. 1A, in accordance with certain embodiments. As shown, a hinge axis and wedge 110 have been planned which will realign the tibia 106 based on the size and location of the cut made through the bone.

Figure 2:
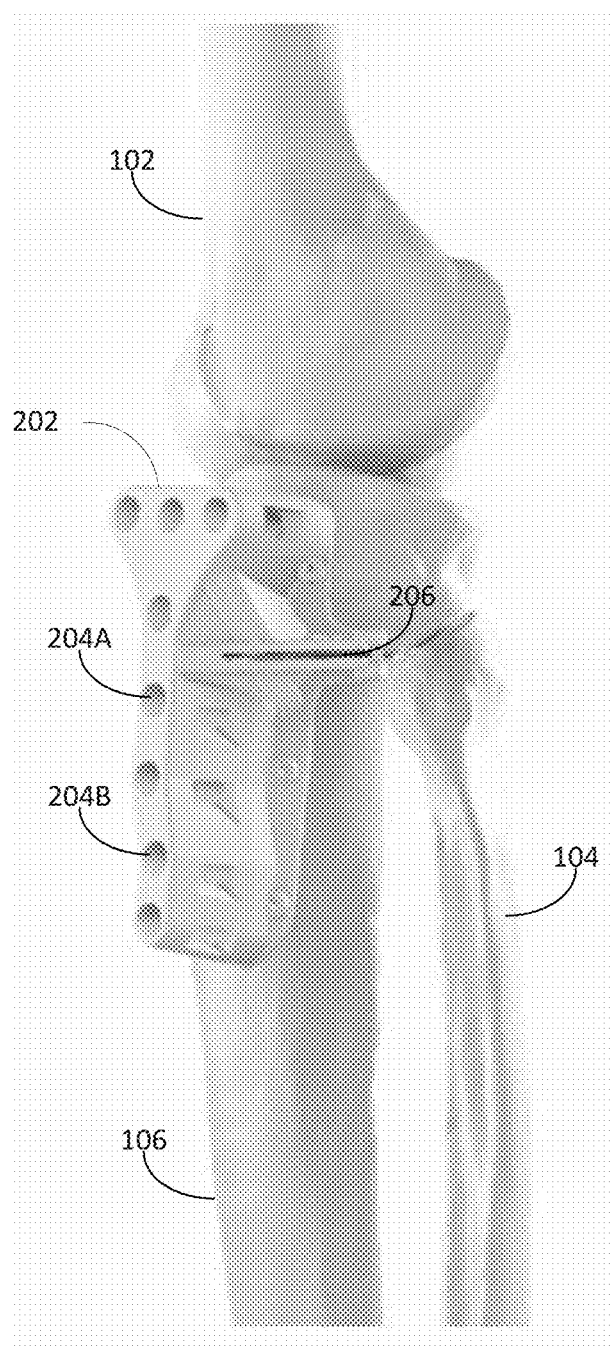
FIG. 2 is an example of an existing bulky single piece osteotomy guide having a large footprint and high profile.

Based on the surgical plan developed based on the measurements and analysis performed in connection with FIGS. 1A and 1B, a patient-specific surgical guide may be designed and manufactured to assist the surgeon in drilling holes and performing the osteotomy cut in the proper location. FIG. 2 provides an illustration of a bulky single-piece patient-specific osteotomy guide 202, which suffers from some of the drawbacks discussed herein. In this example, the patient-specific surgical guide 202 is used in a high tibia osteotomy ("HTO") procedure, and is shown as placed over the bone of the patient. The patient-specific surgical guide 202 may include two types of functional features. The first type of functional feature is one or more drill cylinders such as, for example, drill cylinder 204A and drill cylinder 204B. The drill cylinders may be used for pre-drilling the holes for fixation screws of an osteosynthesis plate. During the procedure, the drill cylinders guide a drill bit into the bone of the patient so that holes for receiving fixation screws through the osteosynthesis plate are located properly, and the osteosynthesis plate is placed in the optimal position on the bone of the patient.

The patient-specific surgical guide 202 may also include one or more cut slots such as cut slot 206. The cut slot 206 may be designed to guide a sawblade into the bone so that the osteotomy cut is both in the proper location and made to the proper depth inside of the bone. Using this guide, the surgeon can pre-drill screw holes before making the osteotomy cut. The inventors have recognized that while the guide shown in FIG. 2 provides a good and stable fit on the bone, in order to achieve that fit and stability, they need a relatively large footprint. This is because the guides need to fit on roughly cylindrical bones, and the guides need to make contact with a large surface area in order to find sufficient bony features that can offer the needed stability. The footprint becomes even larger because it needs to accommodate all the functional features as discussed herein.

The large footprint of the conventional single-piece patient-specific guides such as guide 202 often require that the guide be placed or fitted on regions where surgeons are reluctant to clear soft tissue. In addition, the inventors have discovered that the location of the cut slots, derived from the surgical planning process can often end up being too far in posterior. Existing guides such as guide 202 also provide little visibility on the fitting surface and require, due to their size, a larger incision than is preferred. These factors can result in difficulty in positioning the guide correctly. If the guide is not positioned correctly, deviations from the planned correction may result in the course of carrying out the surgical procedure. The inventors have further recognized that the use of cut slots to guide the osteotomy cut may impose a requirement that a thickness of the sawblade be known during the design of a guide, and also may result in a surgical technique that is dissimilar from traditional osteotomy techniques. Finally, the surgical guide shown in FIG. 2 does not include any features that allow double checking the status of various parameters (e.g. cut positions, bone positions, drill positions, alignments, etc.) during surgery using fluoroscopy, if desired.

Figure 3:
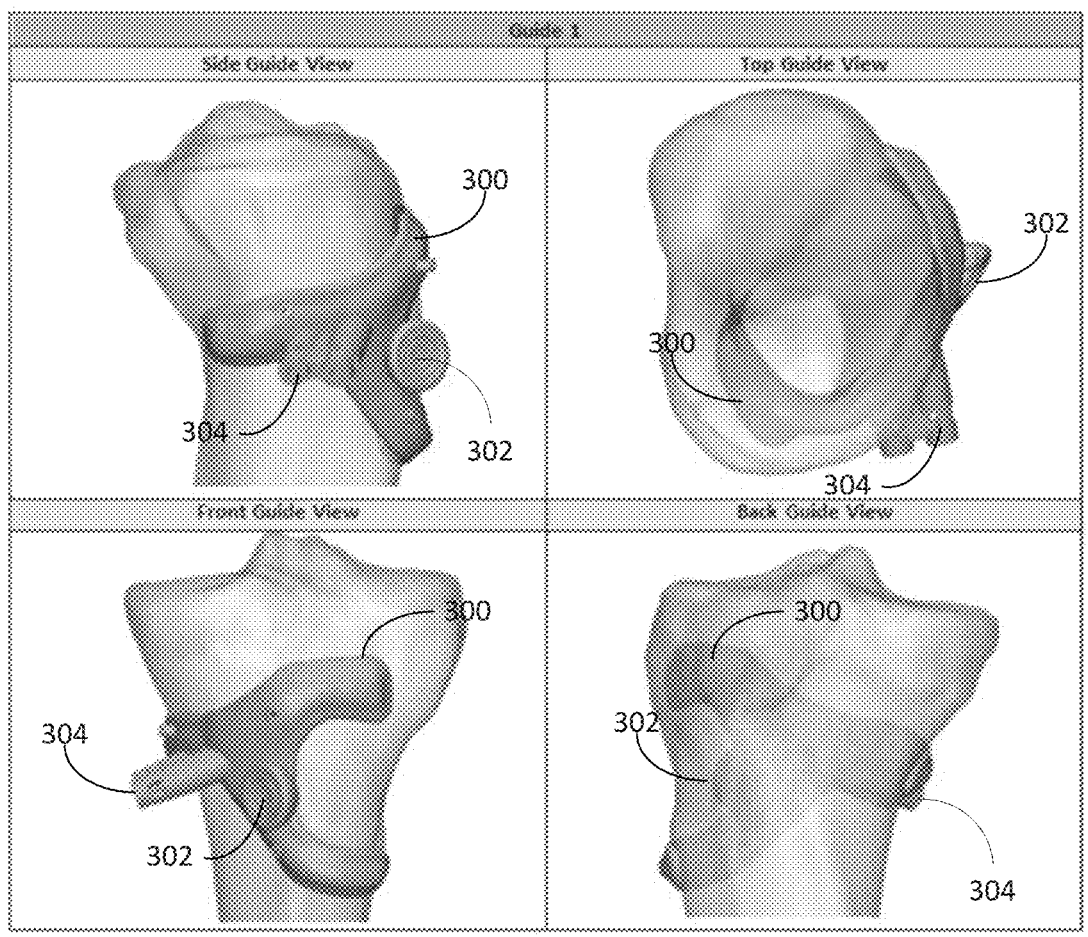
FIG. 3 provides a front, a side, a top, and a back side view of a first guide in a two-part surgical guide, in accordance with certain embodiments.
Figure 4:
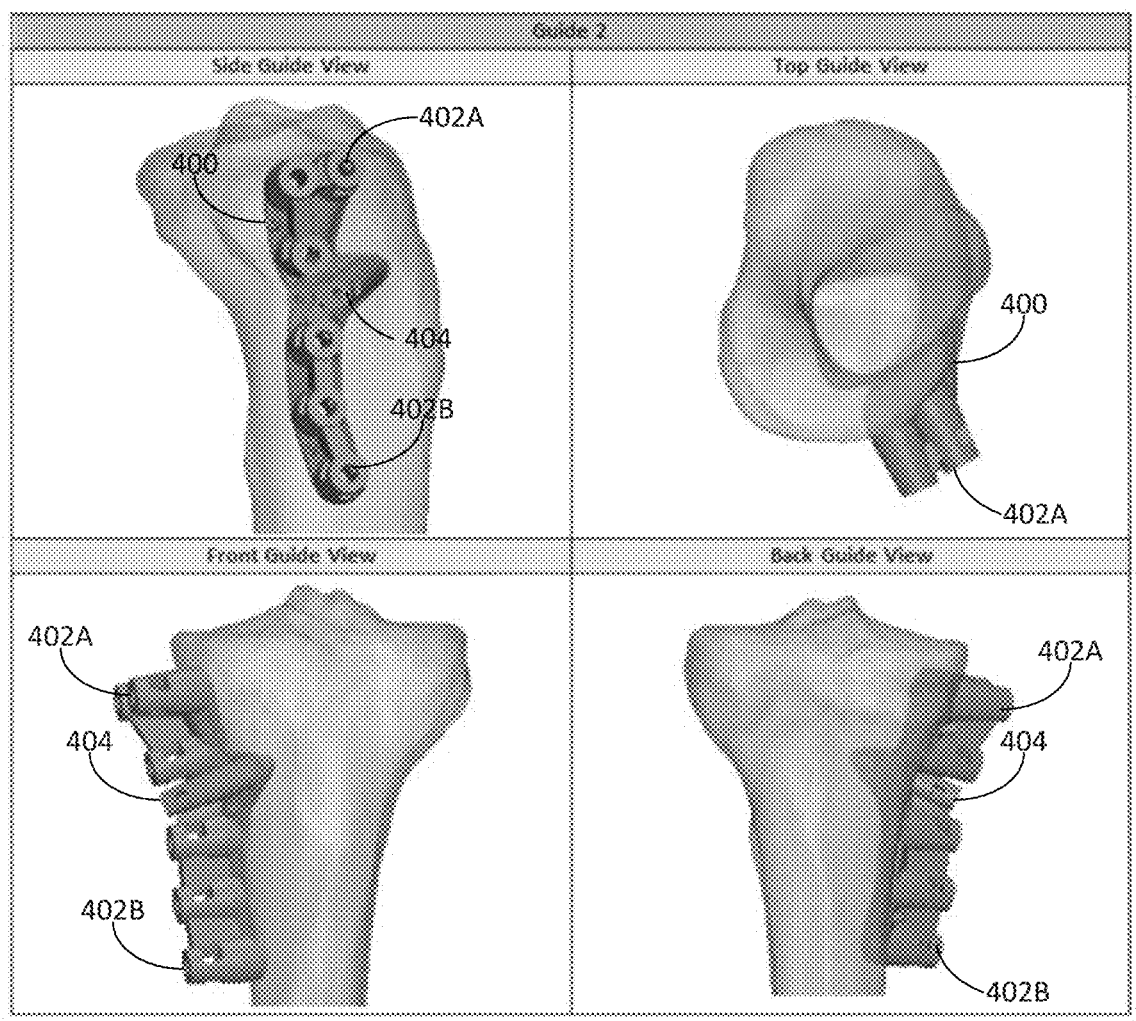
FIG. 4 provides a front, a side, a top, and a back side view of a second guide in a two-part surgical guide, in accordance with certain embodiments.

Having recognized the various problems with existing patient-specific guide designed, the inventors have devised an approach in which two guide parts are used separately, as described herein. FIGS. 3 and 4 provide illustrations of a first part and a second part of a two-part guide which may be used in accordance with one or more embodiments of the invention. As is explained herein, the first guide provides the stability needed to allow the user to position reference pins in the patient's anatomy (e.g. bone), for example along a planned osteotomy plane, while the second guide slides over the reference pins (e.g. guide wires) (using the reference pins for stability) and includes at least one functional element to allow a user to perform a guided procedure on the anatomy of the patient, such as pre-drill the holes for fixation elements (e.g. screws) of an osteosynthesis implant (e.g. an osteosynthesis plate). Further, the reference pins can be used by the surgeon for performing the osteotomy, for example by sliding a sawblade against the reference pins.

FIG. 3 provides a front, a side, a top, and a back side view of a first guide 300 in a two-part surgical guide. In some embodiments, the first guide 300 is an osteotomy guide used for performing an osteotomy. As noted above, both parts of the two-part guide may be manufactured using additive manufacturing technologies such as selective laser sintering or stereolithography. As compared to the guide 202 shown in FIG. 2, the first guide 300 has a significantly smaller footprint in the surgical site. In some embodiments, the first part 300 of the two-part guide includes a push feature 302. The push feature 302 may be used to place the first guide part 300 in the appropriate position on the anatomy of the patient, such as the tibia 106 of a patient. The push feature may be a pressure point feature such as those described in co-owned U.S. Pat. No. 8,984,731, the entire contents of which are hereby incorporated by reference. Unlike the guide 202 from FIG. 2 which has several drill cylinders configured for drilling holes to receive fixation elements to fix an osteosynthesis implant to the bone (e.g. or perform other surgical procedures), the first part 300 of the two-part guide shown in FIG. 3 includes only drill cylinders 304 (e.g. only two drill cylinders) that are used to position guide wires into the bone and not other functional features such as to make cuts or drill holes, such as for fixation elements to fix an osteosynthesis implant to the bone. These drill cylinders 304 are used to drill holes which receive guide wires (such as k-wires, for example), or are used to receive reference pins that directly drill into the patient's anatomy after the first guide part 300 has been placed in the proper location on the bone.

Although not specifically called out in FIG. 3, the bottom surface of the guide part 300 has been designed and manufactured to conform to the surface of the patient's anatomy, such as the tibial anatomy as shown, to ensure a snug and stable fit. However, because this guide part is primarily used only to drill holes for the guide wire through the drill cylinders 304, its footprint can be relatively small. The smaller footprint makes it easier to place the part 300 properly. In some embodiments, use of metal drill sleeves can be abandoned to reduce the size of the drill cylinders even further. Once the guide wire holes have been drilled, the guide wires may be placed into the bone, and the guide part 300 may be slid off of the wires and removed from the surgical site. In some embodiments, guide wires with diamond or trocar tips may be used and drilled directly into the bone. In such embodiments, pre-drilling guide wire holes may not be made in the patient's anatomy.

The second part of the two-part osteotomy guide may be inserted into the patient (e.g. once the first guide part 300 is removed). FIG. 4 provides a front, a side, a top, and a back side view of an exemplary second guide part 400 in a two-part surgical guide according to certain embodiments. Unlike the first guide part 300 which is primarily used for its stability and promotes the necessary precision and accuracy in the location of the guide wires, the second guide part 400 relies more on the guide wires for location and stability. Because the second guide part 400 does not need to rely upon patient anatomy to provide as much stability, its footprint can be reduced. The second guide part 400, supported by the inserted guide wires, provides the necessary drill cylinders (or other functional features) to assist in guiding a procedure on the anatomy of the patient, such as the fixation of an osteosynthesis plate.

In the particular example shown in FIG. 4, the second guide part 400 includes several drill cylinders such as drill cylinders 402A and 402B. These drill cylinders are positioned such that the holes drilled through them will be appropriately spaced to receive fixation elements (e.g. screws) for an osteosynthesis implant (e.g. osteosynthesis plate). The second guide part 400 may be placed onto the patient's anatomy (e.g. tibial anatomy) by sliding the inserted guide wires through the apertures 404 located in the central portion of the guide part 400. As discussed above, this may be the approximate location where the osteotomy cut is to be made. As with the guide part 300, the underneath surface of the second guide part 400 may be manufactured to conform to the anatomical surface of the patient, such as the tibia, to provide further stability when slid over the guide wires.

In some embodiments, such as for a second guide part for a closing wedge osteotomy, the second guide part may include a cut-guiding surface, such as a cut slot. An osteotomy may be performed using the cut-guiding surface for guidance, e.g. by sliding a sawblade along the cut-guiding surface.

In some embodiments, an osteotomy cut may be made using the guide wires to guide the sawblade, e.g. after the second guide part has been removed. Using guide wires instead of a cut slot (as shown in FIG. 2) allows the surgeon to use a more familiar technique.

As discussed herein, the first part of a two-part surgical guide may include one or more contact surfaces that allow for placement of the first part on an anatomical part in a particular position for a snug and secure fit. Such contact surfaces can be determined which allow the first part to fit specifically onto the anatomical part of the patient. Further, in some embodiments, based on a stability analysis thereof the location and extent (e.g. size, number, etc.) of the contact surfaces and the location of a push feature can be evaluated and determined which will allow to optimize positioning and stability of the first part.

Accordingly, in some embodiments, a three-dimensional model of the patient's anatomy to undergo surgery is generated from medical images of the patient such as X-ray, Magnetic Resonance Imaging (MRI), Positron Emission Tomography (PET) scan, Computed Tomography (CT) scan, ultrasound images, etc. A patient-specific first part design can be determined based on the three-dimensional model.

For example, one or more contact surfaces can be determined based on images of the anatomical part of said patient, the three-dimensional model, and/or pre-operative planning of the surgical procedure. Typically, the contact surfaces of the patient-specific first part are patient-specific, i.e. the contact surfaces typically have a shape which is conformal with at least a part of a specific patient's anatomical part.

From the contact surfaces, the stability of the patient-specific first part when there is contact between the contact surfaces and the patient's anatomical part can be determined. The geometric information of the contact surfaces, including the vertex coordinates and unit outward normal vectors of the faces of the contact surfaces can be determined. This geometric information can then be used to characterize the stiffness of the contact between the patient-specific first part and the anatomy. This stiffness can be understood to be the resistance the contact between the patient-specific first part and the anatomy provides towards an externally applied force. The stiffness information can then serve as input for identifying the least-constrained direction of translation and rotation of the patient-specific first part on the anatomical part. In some embodiments, the stiffness information can also serve to evaluate whether other, greater or more suitable contact surfaces should be determined.

More particularly, in some embodiments, the contact surface(s) between the patient-specific first part and the patient's anatomy is identified. Using the points defining this surface and their corresponding unit outward normal vectors, a spatial stiffness matrix of the contact is calculated. Using the eigenvalues of this stiffness matrix, information about the translational and rotational stiffness of the contact can be retrieved. The eigenvectors corresponding to the smallest eigenvalues will define the least-constrained axes of the contact surface.

In this way, in some embodiments, the least-constrained direction for a translation and/or rotation of the patient-specific first part on the anatomical part is determined thereby identifying the optimal direction that force can be applied to the patient-specific first part upon positioning the patient-specific first part on the anatomical part. In some embodiments, this information is used to determine the position and orientation to provide one or more push feature on the design of the patient-specific first part.

Thus, in certain embodiments, a push feature can be included on the patient-specific first part to restrict a possible straight movement over the least-constrained direction of translation. To do this, the force direction of the push feature may be oriented perpendicular to the least-constrained direction of translation. Similarly, in some embodiments, a push feature can be added to the patient-specific first part to restrict a likely rotation around the instantaneous axis of rotation defined by the least-constrained axis of rotation. The functional element may then be positioned such that the force direction is parallel to the least-constrained axis of rotation. In some embodiments, the position of the functional element is as far as possible from the location of instantaneous axis of rotation, to create a maximal restrictive moment applied on the patient-specific first part.

In certain embodiments, the axis of least-constrained direction for rotation and translation can be determined using finite element analysis.

As used herein, the term "push feature" refers to a feature that is provided on the patient-specific first part according to the present methods wherein the push feature allows the user to apply force onto the patient-specific first part. This allows the user to specifically and correctly position the patient-specific first part onto the pre-defined location of the anatomical part. In particular embodiments, it further allows the operator to maintain the position of a patient-specific first part in the correct pre-defined location without any major additional burden for the operator. In particular embodiments, the push feature can also be designed to enhance the application of a force by the user. Typically, the force is a manual force, more particularly a manual force which is created by the operator pushing on the device. The location and orientation of the push feature can be determined in such a way that application of a force thereto ensures stability of the patient-specific first part in the desired orientation. In particular embodiments, the push feature may be a dedicated push feature. In certain embodiments, the push feature may be a handle. In certain embodiments, the push feature may be designed to receive one or more fingers, more particularly finger tips. In further particular embodiments the push feature is a "finger pit".

Figure 5:
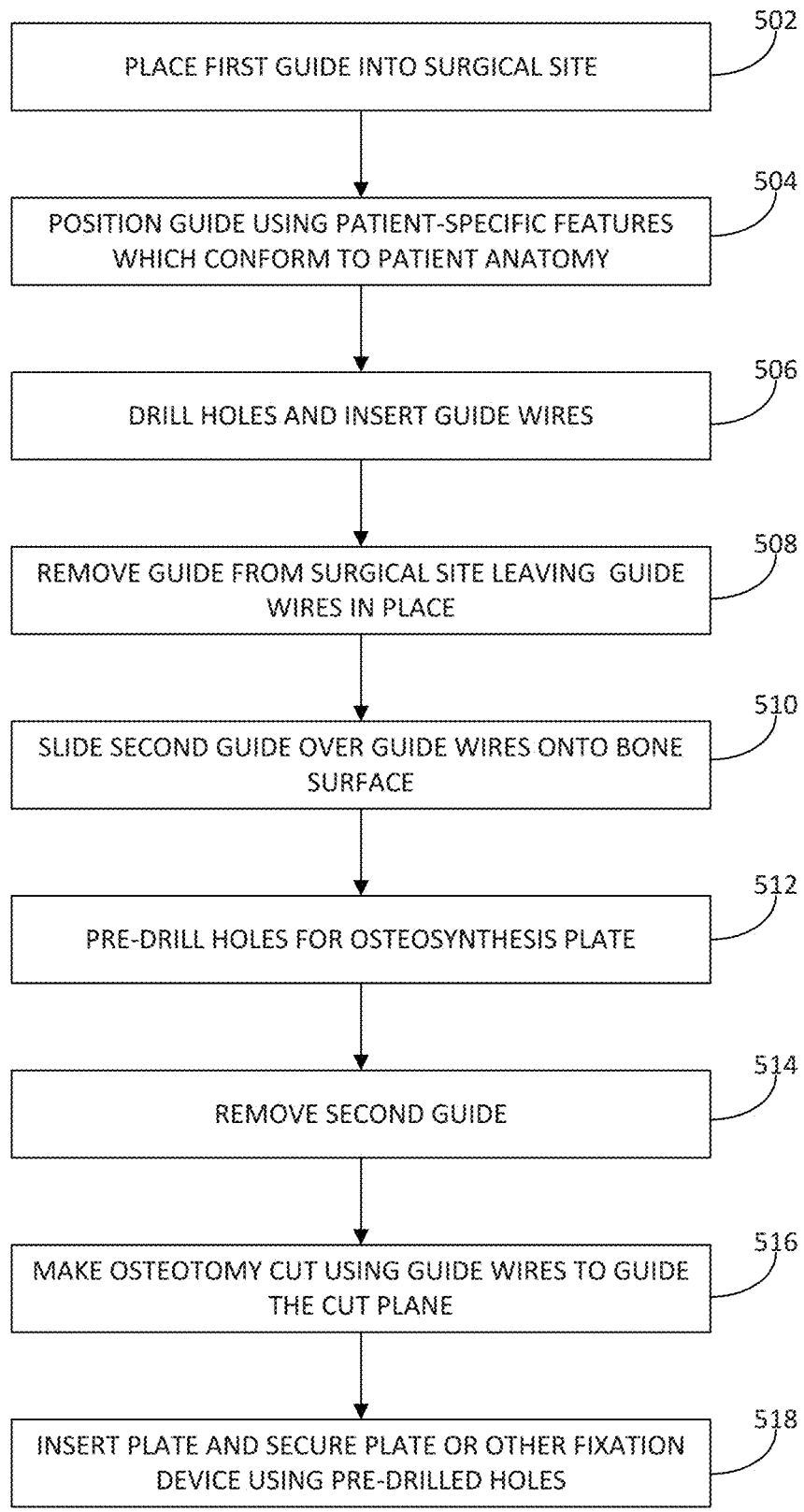
FIG. 5 is a flow chart illustrating a high-level process for performing an osteotomy using a two-part osteotomy guide, in accordance with certain embodiments.

FIG. 5 is a flow chart illustrating a high-level process for performing a surgery using a two-part surgical guide such as the guides shown in FIGS. 3 and 4 above. In particular, FIG. 5 illustrates a process for performing an osteotomy surgery.

The process begins at block 502, where the first part of the two-part guide is placed within the surgical site. As noted above, the first part of the two-part guide may have patient-specific features (e.g. contact surfaces) which conform to at least a portion of the anatomical surface in the patient, such as to substantially restrict movement of the first part with respect to the anatomical surface when positioned on the anatomical surface. Further, at block 504, the first part of the guide is positioned based on the features which conform to the patient's anatomy. In some embodiments, such as where the first part of the guide has a low profile and optionally tapered, rounded or chamfered edges, the first part of the guide can be positioned onto the patient's anatomy by sliding the first part of the guide between a soft tissue and a bone of the patient.

Continuing at block 506, where holes are drilled and guide wires are inserted into the bone. In some embodiments, instead of drilling holes and inserting guide wires into the bone, as discussed, the guide wires may be directly drilled into the bone. Further, in some embodiments, instead of both drilling holes and inserting guide wires into the bone at block 506, only holes may be drilled into the bone at block 506. The guide wires may then be inserted into the bone after the first guide part is removed from the bone (at block 508) and before sliding the second guide part over the guide wires (at block 510). As noted above, the guide may be designed during the planning process described in FIGS. 1A and 1B so that the guide wires are inserted on the plane of the planned osteotomy cut. As further discussed above, the holes may be drilled through drill cylinders (e.g. metal drill cylinders) in some embodiments. Other embodiments may not include them.

Once the guide wires have been inserted, the process may then continue to block 508. At block 508, the first guide part may be removed from the surgical site by backing it out over the guide wires. The guide wires stay in place. In some embodiments, the removal of the first guide part is facilitated by the first guide part having at least one flexible portion that allows the first part to flex so that features which conform to the patient's anatomy and constitute an undercut with respect to the orientation of the guide wires are disengaged from the patient's anatomy while the guide wires stay in place. Next, at block 510, the second part of the two-part osteotomy guide is slid along the guide wires onto the surface of the bone. As noted above, the second guide part may have apertures specifically designed to receive the guide wires, and in doing so, positions the remaining drill cylinders or other functional elements on the second guide part correctly with respect to the patient's anatomy. Next, at block 512, holes for the fixation device (such as an osteosynthesis plate or wedge) are pre-drilled through the drill cylinders of the second guide part. Further, in some embodiments, where the second guide part includes a cut-guiding surface to guide an osteotomy cut, an osteotomy cut is performed using the cut-guiding surface to guide a saw blade (or other cutting device) along the cut plane. Once the holes have been drilled, the second guide part is removed at block 514. Once the second guide part has been removed, at block 516, an osteotomy cut is made using the guide wires to guide a saw blade (or other cutting device) along the cut plane. Once the cut has been made, at block 518, the bone is repositioned and the osteosynthesis plate (or other type of fixation device) is inserted into the patient and secured to the bone using fixation elements (e.g. screws) inserted into the pre-drilled holes.

In certain embodiments, the osteosynthesis plate or other osteosynthesis implant secured to the patient includes a plurality of apertures configured to receive the fixation elements and secure the osteosynthesis implant to the bone. In certain aspects, certain apertures, such as a first aperture, are configured to be positioned at a position on a first side (e.g. top or bottom) of the osteotomy cut (e.g. on a first side of an osteotomy plane corresponding to the osteotomy cut). In certain aspects, certain apertures, such as a second aperture, are configured to be positioned at a position on a second side (e.g. the other of the top or bottom) of the osteotomy cut (e.g. on a second side of an osteotomy plane corresponding to the osteotomy cut). These first and second apertures on the osteosynthesis plate correspond to drilling guides in the second guide part, such that the second guide part can be used to drill holes in the bone to receive the fixation elements that interact with the first and second apertures. Therefore, the first aperture and second aperture, when secured to the bone, are aligned with the positions on the bone corresponding to holes drilled through drill guides of the second guide part.

However, the distance between the first aperture and second aperture on the osteosynthesis plate may not be equal to the distance between the corresponding drill guides on the second guide part for drilling the holes the first aperture and second aperture align with. In particular, as discussed, after the holes are drilled in the bone utilizing the second guide part and the osteotomy cut is made, the portions of the bone on either side of the osteotomy cut may be moved with respect to one another to shorten or lengthen or change the alignment of the bone. Accordingly, the distance between the drilled holes changes as the portions of the bone are moved with respect to one another. The distance between/angle of the first and second aperture in the osteosynthesis implant may therefore be designed to align with the holes drilled in the bone when the portions of the bone are in the desired changed position as opposed to the original position before the surgery. The corresponding drill guides in the second guide part, however, may have a distance between/angle that aligns with the holes drilled in the bone when the portions of the bone are in the original position before the surgery.

Using the two-part guide design described above provides a number of advantages not available in current guides and techniques. By providing less bulky guides, a smaller fitting surface is defined, and a smaller incision may be used (promoting a faster, less painful recovery). In addition, the two-part guide allows for high visibility because its footprint does not block a large portion of the surgical site. Additionally, by using the guide wires to define the cut plane, the surgical technique is closer to osteotomy procedures to which surgeons are accustomed. This results in a shorter learning curve for surgeons. Finally, by using the guide wires, it becomes easier to check status under fluoroscopy, because the guide wires show up on fluoroscopy and are a clear indication of the cutting plane.

The patient-specific two-part surgical guides described herein may be manufacturing utilizing various additive manufacturing and/or three-dimensional (3D) printing systems and techniques. Typically, additive manufacturing techniques start from a digital representation of the 3D object to be formed. Generally, the digital representation is divided into a series of cross-sectional layers, or "slices," which are overlaid to form the object as a whole. The layers represent the 3D object, and may be generated using additive manufacturing modeling software executed by a computing device. For example, the software may include computer-aided design and manufacturing (CAD/CAM) software. Information about the cross-sectional layers of the 3D object may be stored as cross-sectional data. An additive manufacturing (e.g. 3D printing) machine or system utilizes the cross-sectional data for the purpose of building the 3D object on a layer by layer basis. Accordingly, additive manufacturing allows for fabrication of 3D objects directly from computer generated data of the objects, such as computer aided design (CAD) files or STL files. Additive manufacturing provides the ability to quickly manufacture both simple and complex parts without tooling and without the need for assembly of different parts.

Additive manufacturing processes generally include providing energy from an energy source (e.g. a laser, an electron beam, etc.) to solidify (e.g. polymerize) layers of building material (e.g. plastic, metal, etc.). For example, the additive manufacturing machine may selectively apply energy from an energy source to (e.g. scan) the building material based on a job file. The job file may include information regarding slices of a digital representation of an object to be built using an additive manufacturing process.

An additive manufacturing machine builds an object on a layer-by-layer basis by applying energy to (e.g. scanning) the layers of building material according to the scanning pattern for each individual layer as indicated in a job file. For example, the additive manufacturing machine may scan a first layer of physical building material corresponding to a first slice of a digital representation of an object according to the scanning pattern for the first slice. The additive manufacturing machine may then scan a second layer of building material corresponding to a second slice adjacent to the first slice according to the scanning pattern for the second slice. The additive manufacturing machine continues scanning layers of building material corresponding to all the slices in the job file, until the layer corresponding to the last slice is scanned.

Selective laser sintering (LS) is an additive manufacturing technique used for 3D printing objects. LS apparatuses often use a high-powered laser (e.g. a carbon dioxide laser) to "sinter" (i.e. fuse) small particles of plastic, metal, ceramic, glass powders, or other appropriate materials into a 3D object. The LS apparatus may use a laser to scan cross-sections on the surface of a powder bed in accordance with a CAD design or job file. Also, the LS apparatus may lower a manufacturing platform by one layer thickness after a layer has been completed and add a new layer of material in order that a new layer can be formed. In some embodiments, an LS apparatus may preheat the powder in order to make it easier for the laser to raise the temperature during the sintering process.

Figure 6:
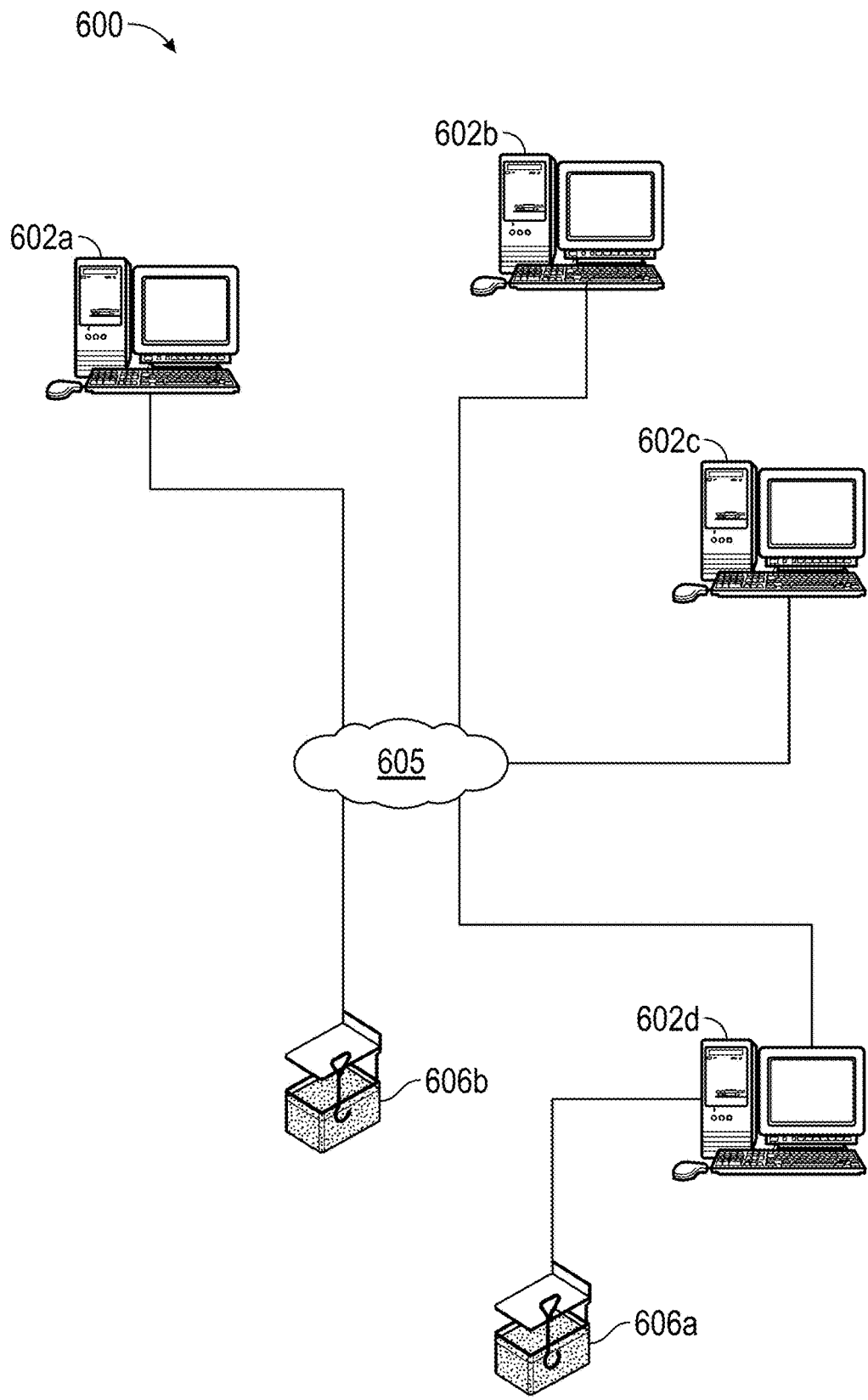
FIG. 6 is an example of a system for designing and manufacturing 3D objects.

Embodiments of the invention, including two-part surgical guides, may be designed and manufactured within a system for designing and manufacturing 3D objects. Turning to FIG. 6, an example of a computer environment suitable for the implementation of 3D object design and manufacturing is shown. The environment includes a system 600. The system 600 includes one or more computers 602a-602d, which can be, for example, any workstation, server, or other computing device capable of processing information. In some aspects, each of the computers 602a-602d can be connected, by any suitable communications technology (e.g. an internet protocol), to a network 605 (e.g. the Internet). Accordingly, the computers 602a-602d may transmit and receive information (e.g. software, digital representations of 3-D objects, commands or instructions to operate an additive manufacturing device, etc.) between each other via the network 605.

The system 600 further includes one or more additive manufacturing devices (e.g. 3-D printers) 606a-606b. As shown the additive manufacturing device 606*a* is directly connected to a computer 602*d* (and through computer 602*d* connected to computers 602*a*-602*c* via the network 605) and additive manufacturing device 606*b* is connected to the computers 602*a*-602*d* via the network 605. Accordingly, one of skill in the art will understand that an additive manufacturing device 606 may be directly connected to a computer 602, connected to a computer 602 via a network 605, and/or connected to a computer 602 via another computer 602 and the network 605.

It should be noted that though the system 600 is described with respect to a network and one or more computers, the techniques described herein also apply to a single computer 602, which may be directly connected to an additive manufacturing device 606. Any of the computers 602*a*-602*d* may be configured to design and/or manufacture two-part surgical guides as described herein.

Figure 7:
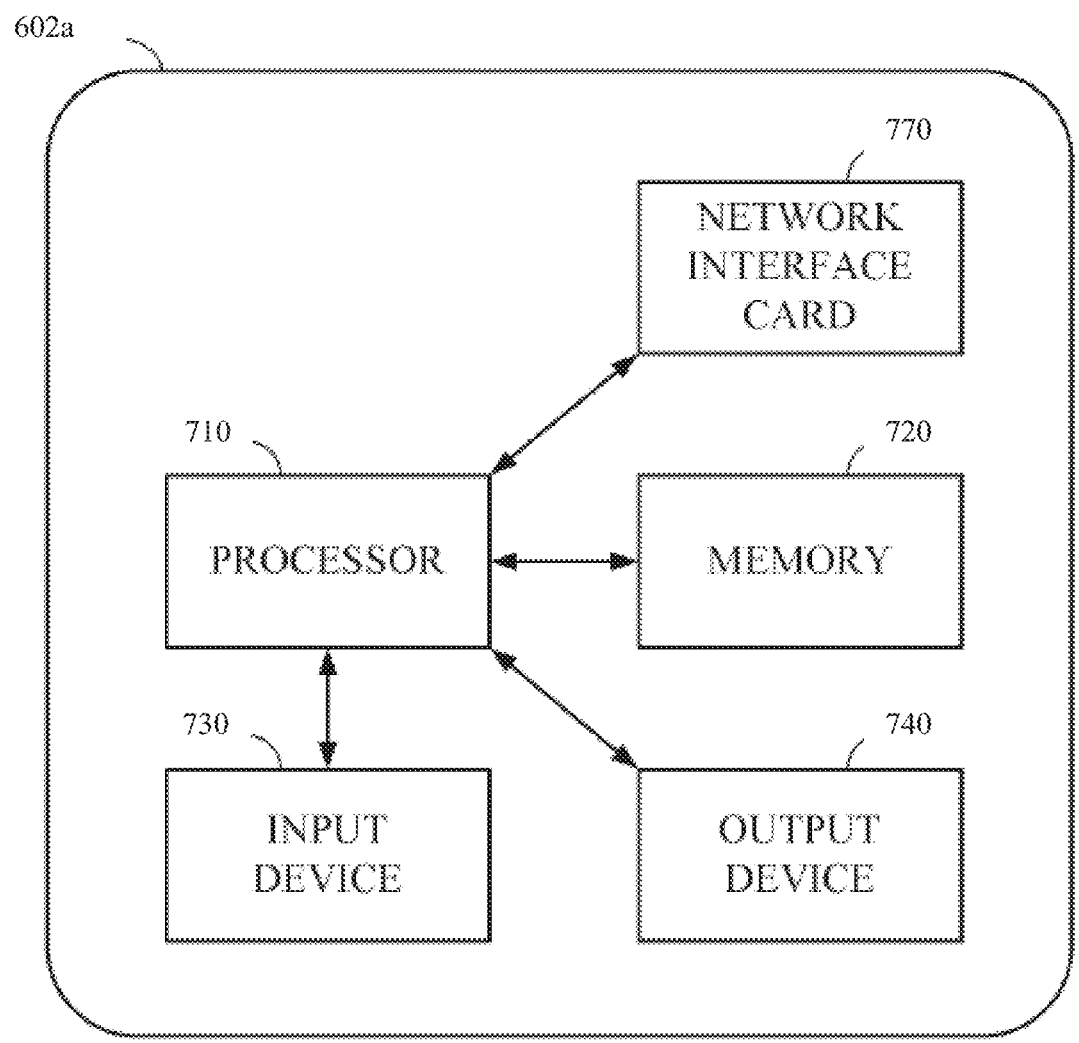
FIG. 7 illustrates a functional block diagram of one example of the computer shown in FIG. 6.

FIG. 7 illustrates a functional block diagram of one example of a computer of FIG. 6. The computer 602*a* includes a processor 710 in data communication with a memory 720, an input device 730, and an output device 740. In some embodiments, the processor is further in data communication with an optional network interface card 770. Although described separately, it is to be appreciated that functional blocks described with respect to the computer 602*a* need not be separate structural elements. For example, the processor 710 and memory 720 may be embodied in a single chip.

The processor 710 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g. a combination of a DSP and a microprocessor, a plurality of microprocessors, one or more microprocessors in conjunction with a DSP core, or any other such configuration.

The processor 710 can be coupled, via one or more buses, to read information from or write information to memory 720. The processor may additionally, or in the alternative, contain memory, such as processor registers. The memory 720 can include processor cache, including a multi-level hierarchical cache in which different levels have different capacities and access speeds. The memory 720 can also include random access memory (RAM), other volatile storage devices, or non-volatile storage devices. The storage can include hard drives, optical discs, such as compact discs (CDs) or digital video discs (DVDs), flash memory, floppy discs, magnetic tape, and Zip drives.

The processor 710 also may be coupled to an input device 730 and an output device 740 for, respectively, receiving input from and providing output to a user of the computer 602*a*. Suitable input devices include, but are not limited to, a keyboard, buttons, keys, switches, a pointing device, a mouse, a joystick, a remote control, an infrared detector, a bar code reader, a scanner, a video camera (possibly coupled with video processing software to, e.g. detect hand gestures or facial gestures), a motion detector, or a microphone (possibly coupled to audio processing software to, e.g. detect voice commands). Suitable output devices include, but are not limited to, visual output devices, including displays and printers, audio output devices, including speakers, headphones, earphones, and alarms, additive manufacturing devices, and haptic output devices.

The processor 710 further may be coupled to a network interface card 770. The network interface card 770 prepares data generated by the processor 710 for transmission via a network according to one or more data transmission protocols. The network interface card 770 also decodes data received via a network according to one or more data transmission protocols. The network interface card 770 can include a transmitter, receiver, or both. In other embodiments, the transmitter and receiver can be two separate components. The network interface card 770, can be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform certain functions described herein.

Figure 8:
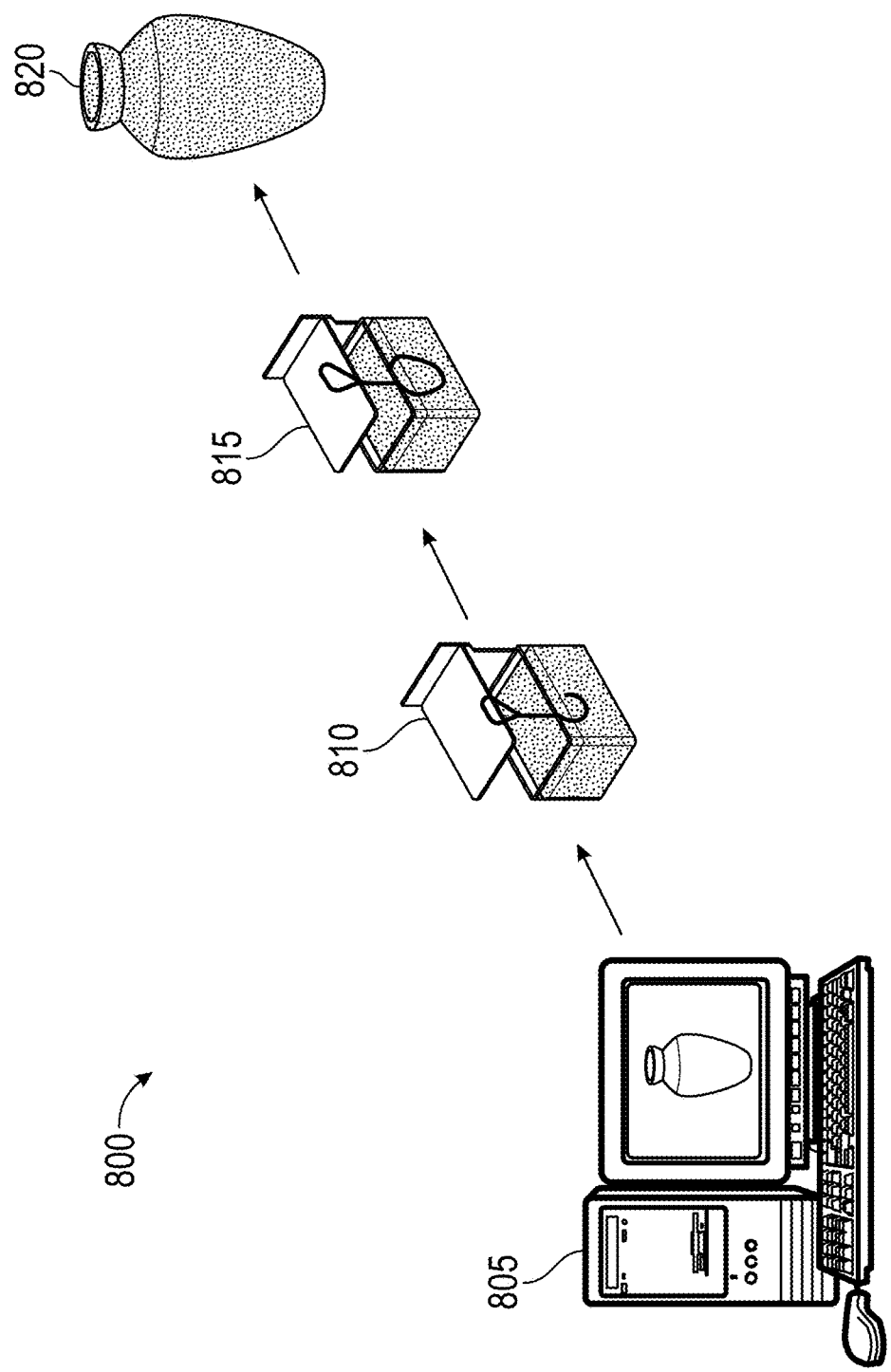
FIG. 8 shows a high-level process for manufacturing a 3D object using an additive manufacturing system.

FIG. 8 illustrates a process 800 for manufacturing a 3-D object or device. As shown, at a step 805, a digital representation of the object is designed using a computer, such as the computer 602*a*. For example, 2-D or 3-D data may be input to the computer 602*a* for aiding in designing the digital representation of the 3-D object. Continuing at a step 810, information is sent from the computer 602*a* to an additive manufacturing device, such as additive manufacturing device 606, and the device 606 commences the manufacturing process in accordance with the received information. At a step 815, the additive manufacturing device 606 continues manufacturing the 3-D object using suitable materials, such as a liquid resin. At a step 820, the object is finally built.

These suitable materials may include, but are not limited to a photopolymer resin, polyurethane, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESD7, ABS-M30, ABS-M30i, PC-ABS, PC ISO, PC, ULTEM 9085, PPSF and PPSU materials from Stratasys; Accura Plastic, DuraForm, CastForm, Laserform and VisiJet line of materials from 3-Systems; the PA line of materials, PrimeCast and PrimePart materials and Alumide and CarbonMide from EOS GmbH. The VisiJet line of materials from 3-Systems may include Visijet Flex, Visijet Tough, Visijet Clear, Visijet HiTemp, Visijet e-stone, Visijet Black, Visijet Jewel, Visijet FTI, etc. Examples of other materials may include Objet materials, such as Objet Fullcure, Objet Veroclear, Objet Digital Materials, Objet Duruswhite, Objet Tangoblack, Objet Tangoplus, Objet Tangoblackplus, etc. Another example of materials may include materials from the Renshape 5000 and 7800 series.

Various embodiments disclosed herein provide for the use of a controller or computer control system. A skilled artisan will readily appreciate that these embodiments may be implemented using numerous different types of computing devices, including both general-purpose and/or special-purpose computing-system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general-purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special-purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

The human skeleton is composed of a large number of individual bones that perform a variety of important functions, including support, movement, protection, storage of minerals, and formation of blood cells. In response to trauma bones of the skeleton may become fractured. To ensure that the skeleton retains its ability to perform its important functions and to reduce pain and disfigurement, fractured bones should be repaired promptly and properly. Typically, fractured bones are treated using fixation devices, which reinforce the fractured bones and keep them aligned during healing. Fixation devices may take a variety of forms, including casts for external fixation and bone plates for internal fixation. Casts are minimally invasive, allowing reduction and fixation of simple fractures from outside the body. In contrast, bone plates are sturdy internal devices that are mounted directly onto the bone(s) adjacent to the fracture.

Some bone defects (such as hallux valgus, coxa vara, genu valgum, and genu varum) are treated by an osteotomy, i.e. a surgical intervention involving cutting of the bone in order to shorten the bone, lengthen it or change its alignment. After surgery a bone plate is often used to hold the remaining detached bone fragments in their desired position for healing.

Bone plates generally provide a rigid structure comprising openings through which bone fixation elements are inserted into the bone to anchor the plate to the target portions of the bone. The bone plate is fastened to opposite sides of the fracture or surgical cut using suitable fixation elements, such as screws and/or wires, so that the bone fragments are fixed in position. The mounted plate may be left in place permanently, or it may be removed after the bone has healed sufficiently.

Bone plates are available in different sizes such that the surgeon can choose a bone plate adapted to the size of the fracture and/or disconnected bone fragments during the surgical procedure. However, the shape of the bone plates from which the surgeon can choose is limited, as the currently available bone plates typically have a generic shape. A suboptimal fit of the bone plate however may negatively affect the healing process.

Another problem often encountered during these types of orthopedic procedures is that during the fixation of the bone plate the fracture dislocates or repositions slightly due to the forces required for inserting the fixation elements into the bones for fastening the bone plate. As there is almost no opportunity during the surgical procedure to loosen the fixation elements in order to reposition the fracture for optimal healing, small dislocations are often left, leading to suboptimal healing of the fracture and possible complications during or after the healing process.

Accordingly, there is a need for improved ways to repair structural defects in the field of orthopedic surgery.

The disclosed systems and methods as described herein will be described with respect to particular embodiments but the systems and methods are not limited thereto.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of when referring to recited members, elements or method steps also include embodiments which "consist of said recited members, elements or method steps.

Furthermore, the terms first, second, third and the like in the description, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

All documents cited in the present specification are hereby incorporated by reference in their entirety.

Unless otherwise defined, all terms used herein, including technical and scientific terms, have the meaning as commonly understood by one of ordinary skill in the art. By means of further guidance, definitions for the terms used in the description are included to better appreciate the present teaching. The terms or definitions used herein are provided solely to aid in the understanding of the present disclosure.

Reference throughout this specification to "one embodiment" or "an embodiment" means that a particular feature, structure or characteristic described in connection with the embodiment is included in at least one embodiment as disclosed herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the present scope, and form different embodiments, as would be understood by those in the art.

Provided herewith are systems, including apparatuses and methods which may be used for performing a surgical orthopedic intervention requiring the installation of a bone plate, allowing the surgeon to perform the orthopedic intervention according to a preoperative plan to ensure accuracy of the intervention such that the amount of time the patient is in surgery is minimized and the post-operative healing process is optimized. The orthopedic systems can be patient-specific.

A first aspect relates to a bone plate for use in the context of orthopedic surgery. The bone plate is used for fixating two or more bone fragments according to a preoperative plan. A bone fragment as used herein refers to partially or completely separated parts originating from one bone. The bone plate ensures that the bone fragments are fixed in a predetermined position relative to each other to assist in the healing and/or to stabilize damaged or weakened bones or portions of bone.

The bone plate provides a rigid structure which is typically (but not necessarily) longitudinal in order to span over a gap (caused by fracture and/or osteotomy) between two bone fragments or over a stretch of weakened bone. The rigid structure, also referred to as supporting element, is such that, after attachment to the bone or bone fragments it can maintain these in position even under stress conditions.

The rigid structure of the bone plate typically comprises one or more patient-specific features, which allow positioning of the bone plate onto at least one bone fragment in a specific position which position is determined based on pre-operative planning. The one or more patient-specific features typically match features and/or areas of the bone or bone fragment(s) and help guide the placement of the bone plate and ensure a unique fit thereof. In particular embodiments the bone plate is envisaged for fixing two bone fragments to each other and comprises at least two patient-specific features, each corresponding to or matching a feature on one of the bone fragments which are to be fixed together whereby the features are selected such that in the pre-operatively determined relative position of the bone fragments, the features on the bone plate will optimally match the corresponding features on the bone fragments. Thus, the patient-specific features will help ensure that the bone plate fixes the bone fragments according to the pre-operative planning.

The rigid structure or supporting element of the bone plate may have a standard thickness or may be provided in a particular embodiment with a varying thickness. More particularly, the thickness of the supporting element may be locally increased for instance around the osteotomy or fracture plane, thereby to providing the bone plate with a higher stress resistance.

The patient-specific features provided on the bone plate are typically selected from patient-specific surfaces (matching a specific surface structure on the bone), combinations of specifically placed holding pins (corresponding to a specific shape of the bone), etc.

The bone plate further comprises fixation features for fixing the bone plate onto the bone or bone fragments. The fixation features typically comprise openings in the bone plate through which bone fixation elements, such as pins, but more particularly threaded elements such as screws can be inserted into the bone to anchor the bone plate to the bone.

In particular embodiments, the bone plate further comprises positioning elements which aid the positioning of the bone plate onto the bone. The positioning elements that are provided onto the bone plate may be any means which allow a first positioning of the bone plate onto the bone. In a particular embodiment, these positioning elements are non-threaded structures such as, but not limited to pins, pegs or hooks. The bone plates are typically provided with at least one positioning element, which is provided (or envisaged to be provided) on a part of the bone plate envisaged to be positioned on one of the bone fragments (where the fixation of more than one bone fragment is envisaged) or on one area of the bone. In particular embodiments, the bone plate comprises at least two positioning elements, the first positioning element being located on one bone fragment or part of the bone adjacent the bone defect or cut and the second positioning element being located on the other bone fragment or bone area adjacent to the bone defect or cut.

In particular embodiments however, one or more of the positioning elements may be non-threaded apertures such as, but not limited to holes for pins, pegs or hooks. Where the positioning element on the plate is a hole (extending through the rigid structure of the bone plate) for a pin peg or hook, this is intended for use with a corresponding external positioning device, such as a pin, peg or hook, which can be introduced through the bone plate into the bone upon positioning the bone plate. Typically, the position and orientation of the hole or opening will determine the orientation of the positioning device in the bone. Additionally or alternatively, in particular embodiments, the positioning element may be a structure extending from the rigid structure of the bone plate, which can be introduced into bone when positioning the bone plate onto a bone fragment e.g. by exerting pressure onto the bone plate. In these embodiments, the positioning element may have a pin, peg or hook-like shape extending from the bone plate (more particularly from the surface intended to be positioned on the bone, i.e. the same surface of the bone plate comprising the patient-specific feature(s)). Typically, as the bone plate is typically designed to be positioned parallel to the bone surface, the (external or incorporated) positioning elements/devices may be positioned perpendicular to the bone surface. This may imply that the positioning elements/devices intended for introducing into the bone are all positioned essentially perpendicular to the surface of the bone plate and to the surface of the bone. In particular embodiments, at least two of the positioning elements/devices are such that these elements/devices for introducing into the bone are positioned in parallel relative to each other. In further particular embodiments all positioning elements/devices of said bone plate are positioned parallel relative to each other. However, it is also envisioned that the positioning elements or external positioning devices are provided on the bone plate so as not to be positioned parallel to each other. This may increase the stability of the bone plate on the bone. In particular embodiments, the positioning elements are envisaged to be oriented at a slight angle (2-10°) with respect to the axis perpendicular to the bone surface. In particular embodiments, the orientation of this angle is different for the different positioning elements/devices. Where the positioning elements are openings which allow the introduction of external positioning devices, the openings can be provided such that they allow and/or ensure non-parallel introduction of external positioning devices. The same applies to the fixation features and their respective fixation elements.

In particular embodiments the positioning elements of said bone plate are detachable and removable, thereby allowing a first set of less permanent positioning elements to be removed and replaced by more permanent fixation elements. Thus, in particular embodiments, the positioning elements may function as fixation features. For instance, when pegs are used as positioning elements or positioning devices, after the positioning of the bone plate into the correct position and a first fixation of the bone plate to the bone, one may envisage removing the pegs from the bone plate and introducing further screws as fixation elements to further strengthen the position of the bone plate. In particular embodiments as detailed above, the bone plate is thus provided with a combination of fixed positioning elements on the bone plate which are openings and separate external positioning devices and fixation elements which can be inserted there through.

It will be understood that the bone plates are tailored specifically for the repair of the bone defect or osteotomy at hand. In particular embodiments, not only patient-specific features are provided, but the size of the bone plate and the position and orientation of the different positioning elements and fixation features are determined according to a preoperative plan.

According to particular embodiments, a multitude of 3, 4, 5, 6, 7, 8 or more fixation features and/or positioning elements can be provided on the bone plate, depending on the complexity of the bone defect (where multiple parts are to be fixated relative to each other with one bone plate) or where for instance a higher degree of strength is required.

The present disclosure further envisages methods for fixing bone fragments according to a predetermined position using the bone plates as disclosed herein.

These methods typically involve the step of drilling holes into the bone or bone fragments, for receiving the positioning elements and/or the fixation elements introduced through the fixation features of the bone plate. Thus, holes to receive these positioning elements and/or fixation elements are drilled into the bone or bone fragments according to a pre-operatively planned position of the bone plate. Drilling of the holes is typically ensured using a guide.

Where the bone plate as disclosed herein is envisaged for use in an osteotomy procedure of an intact bone, e.g. for removing part of the bone, drilling of the holes can be ensured prior to the osteotomy step, i.e. when the bone is still in one piece. Alternatively, drilling can be ensured after the osteotomy is performed, on each of the bone fragments.

Thereafter, the bone plate is positioned on one of the bone fragments. More particularly, the part of the bone plate envisaged for placement on that bone fragment.

In particular embodiments, the bone plate is provided with at least one patient-specific feature matching an area of that bone fragment to which the bone plate is attached first. More particularly, the patient-specific feature matches an area of the bone fragment to which the bone plate is first attached near or adjacent to the areas where the positioning elements and/or fixation elements are or will be introduced into the bone fragment. By providing patient-specific features near areas where positioning elements and/or fixation elements are introduced, the surgeon manipulating and positioning the patient-specific bone plate is ensured that the bone plate is fixed in the correct position when fixing the bone plate onto the patient's anatomy.

In particular embodiments, after the bone plate has been fixed onto the first bone fragment, the two or more bone fragments are repositioned into the correct position for healing, using the bone plate fixated onto one of the bone fragments as a hinge to aid the surgeon. Where the bone plate comprises a further patient-specific feature corresponding to/matching a feature on the surface of the second bone fragment, the correct fit of the bone plate on the second bone fragment will be aided by matching the patient-specific feature with the corresponding feature on the bone.

Once the bones are placed in the correct relative position for healing the fixation elements can be introduced into the fixation features on the bone plate through the bone, thereby fixating the position of the reconstituted bone defect in the correct position for optimal healing.

As the bone plate is used as a hinge for repositioning the bone fragments into to their correct relative position for healing, it may be necessary to ensure a fixation to the first bone fragment which is sufficiently strong. The provision of multiple positioning elements on the bone fragment to which the bone plate is first attached provide an increased strength of the attachment and allows the surgeon to put more pressure on the bone plate which functions as a hinge. Accordingly, the number of positioning elements on either side of the bone plate may be unequal, thereby providing N+X positioning elements on the side of the bone plate which is fixated first to the bone fragment and providing N positioning elements on the side of the bone plate which is fixated once the bone defect is repositioned into the correct position for healing. N being an integer equal to 1, 2, 3, 4, 5, 6, 7, 8 or more and X being an integer equal to 1, 2, 3, 4, 5, 6, 7, 8 or more. In particular embodiments the positioning elements are an integral part of the bone plate.

Once the bone fragments are repositioned and the bone plate is fixated into the correct position using the positioning elements, the bone plate is fastened to the different bone fragments using suitable fixation elements. Suitable fixation elements include any type of fixation or attachment elements as can be envisaged by a skilled person, including, but not limited to screw, nails, bolts, pins, clamps or stitches, to ensure that the bone plate is definitively fixed into position.

As described above, the bone plate comprises fixation features such as openings through which bone fixation elements can be inserted into the bone to definitely anchor the bone plate to each of the bone fragments. As the bone plate is already fixated into the correct position (by the positioning elements), the further fixation using stronger and more permanent fixation elements will not have an effect on the position of the reconstituted bone, thereby ensuring that the correct position for healing is maintained also after fixating the bone plate permanently. The mounted bone plate may be left in place permanently, or it may be removed after the bone has healed sufficiently.

It is noted that typically the bone plate as disclosed herein is a one piece structure optionally with separate or detachable fixation and/or positioning elements.

In an alternative embodiment the bone plate is provided in two or more separate parts, which can be combined and attached to each other to form a one-piece bone plate after placement on the bone fragments. In these embodiments, the complete bone plate (i.e. when both parts are joined) is designed according to pre-operative planning to ensure correct positioning of the different bone fragments relative to each other. The bone plate is however provided in two parts, each of which can be attached to a bone fragment in a specific position (optionally guided by one or more patient-specific features). Thereafter, connecting of the two parts of the bone plate (to generate a single base plate structure) will ensure that the corresponding bone fragments are correctly positioned.

In particular embodiments the separate parts of the bone plate each comprise positioning elements. In these embodiments, the two parts of the bone plate can be referred to as positioning parts. In further particular embodiments, a positioning part comprises positioning elements provided with a patient-specific feature, ensuring/aiding the correct positioning of the positioning part onto a bone fragment. Typically, the positioning parts further comprise attachment elements to which a bone connector can be attached for connection of one positioning part to another.

Where the bone plate is provided as separate positioning parts, placement will typically first involve positioning of a positioning part on the bone and a first fixation by positioning elements. Typically, each of the two positioning parts is provided onto a different bone fragment. After inserting the positioning elements into the bone fragments, the bone fragments can be repositioned into the correct position relative to each other for healing. In a next step, the bone connector is attached to each of the positioning parts, thereby forming a bone plate as disclosed herein. By using a bone plate comprising separate parts which can be interconnected, the bone plate can be assembled by the surgeon during the surgical procedure, allowing the surgery to occur in a small surgical window, leading to a faster healing process. The assembly of the different parts is easily performed by the surgeon. In particular embodiments, the correct position of the bones for healing is ensured by the patient-specific character of each of the positioning parts of the bone plate.

The present disclosure further relates to methods for generating bone plates providing a tailored and defect-specific approach as each bone plates is made on the basis of the specific defective bone at hand and its envisaged repair.

Typically, the bone plate is developed by first generating a two dimensional (2D) or three dimensional (3D) model of the bone defect or envisaged osteotomy based on one or more images thereof, generating a 2D or 3D model of the envisaged repair of the bone defect or result of the osteotomy and generating a bone plate matching or corresponding to at least part of the surface of the bone fragments surrounding the area. Optionally, the bone plate is further provided with positioning elements. In further particular embodiments, the bone plate is provided with openings for fixation elements.

Accordingly, herein disclosed are methods of making a bone plate for fixing a bone defect, the method comprising the steps of: generating a 2D or 3D model of the bone defect or envisaged osteotomy based on one or more images of the bone and the surgical plan; designing based on said 2D or 3D model a model corresponding to the envisioned repair of said bone defect/envisaged result of the osteotomy; generating a bone plate with a rigid structure based on the information above comprising: one or more patient-specific features matching or corresponding to the surface of a bone fragment in the area close to the defect or osteotomy, and fixation features in areas suitable for fixing the bone plate to each of said bone fragments.

More particularly the methods for making a bone plate for fixing a bone defect may further comprise steps of returning to the model of the bone fragments prior to the envisaged repair (the original position of the bone fragments), taking into account the axis depth of the positioning and/or fixation elements of said bone plate, and generating a guide comprising drill-guides for drilling holes in to the bone fragments to receive the positioning and/or fixation elements of said bone plate. More particularly, said drill holes are predrill screw holes.

Thus, the methods as disclosed herein rely on one or more images of the bone defect or of the bone for which osteotomy is envisaged. In particular embodiments, the methods as disclosed herein include the step of taking images of the bone or bone defect. The images may be any type of image that can be used to create a 2D or 3D image or model of said envisaged repair of the bone or result of the osteotomy. It is not required that the images are of the entire patient. Indeed, typically, only part of the patient is reflected in the image, provided that this part also includes the area of the bone defect.

In particular embodiments, the images are 2D or 3D images. The images can be taken using any type of imaging apparatus or imaging technique which allows imaging or scanning the defective object in an accurate manner. These may include equipment such as cameras and scanners for industrial, household or medical use. In particular embodiments the imaging techniques and appliances used are typical medical imaging tools such as, but not limited to radiography, X-ray, ultrasound or fluoroscopy for 2D images and computer tomography (CT) scans, magnetic resonance imaging (MRI) scans for 3D images. It is noted that from a combination of 2D images a 3D model can be constituted (according to U.S. 61/579,927 which is incorporated herein by reference). A summary of medical imaging has been described in "Fundamentals of Medical imaging", by P. Suetens, Cambridge University Press, 2002.

The term "medical imaging" as used herein refers to techniques and processes used to create images of the human or animal body (or parts and function thereof), typically for clinical purposes (medical procedures seeking to reveal, diagnose or examine disease) or medical science (including the study of normal anatomy and physiology).

Based on these images, a 2D or 3D model of the objects defective region is made. This 2D or 3D model allows a detailed analysis of the bone defect to determine the actual size and shape of the defect. The examination of the defect allows the reconstitution of the bone defect to its original position and/or the provision of the desired repair of the defect.

In particular embodiments, the methods involve performing virtual surgery on the defective bone to identify the defect site and determining the shape and/or form parameters of the defect or of the structure necessary to fix the defect. Based thereon, a model corresponding to the envisioned repair of said bone defect or osteotomy is generated. This can be obtained by manual designing based on anatomical knowledge. This involves determining the optimal position of the remaining elements relative to each other. Where the bone is a long bone, typically, the defect or osteotomy will generate two parts which need to be fixed in a specific position relative to each other. In other embodiments, such as fractures of the skull, the optimal position of multiple pieces may need to be determined.

In a next step the bone plate is generated based on the model corresponding to the envisioned repair of said bone defect or envisaged osteotomy. In particular embodiments, the bone plate is designed to comprise patient-specific features matching or corresponding to the surface of said model for one or more, and typically for each of the bone fragments. Additionally, the positions of the different positioning elements and openings for fixation elements (also referred to herein as fixation features) corresponding to suitable positions in each of the bone fragments which are to be fixed to each other is also determined. The methods as disclosed herein are envisaged e.g. in the context of orthopedic surgery. The model will allow the identification of areas on the bone fragments (typically in the vicinity of the defect) that are suitable for fixing and/or attaching the bone plate.

The bone plate can be made based on the information for these different features.

Typically, the methods allow the generation of a specifically fitting bone plate. Most particularly, the methods envisage making the bone plate in one piece or in separate detachable parts. Methods of manufacturing will be detailed below.

The step of generating said bone plate may thus include designing a model of a bone plate or an image thereof. The design of the bone plate may further be provided on an information carrier or can be sent to a manufacturing facility for the manufacturing of the bone plate or parts thereof. Thus, in particular embodiments, the methods as disclosed herein include manufacturing the bone plate or parts thereof.

As detailed above, the methods envisage the generation of a bone plate comprising one or more surfaces that fit specifically with the bone fragment(s). In particular embodiments, the bone plates may comprise one or more free-form structures fitting at least part of the surface of the bone fragments. The term "free-form structure" as used herein refers to a structure having an irregular and/or asymmetrical flowing shape or contour, more particularly fitting at least part of the contour of the bone fragments. Thus, in particular embodiments, the free-form structure is a free-form surface, as described above. A free-form surface refers to an (essentially) 2D shape contained in a 3D geometric space. Indeed, as will be detailed below, such a surface can be considered as essentially 2D but may have a varying thickness. Typically, the free-form structure or surface is characterized by a lack of rigid radial dimensions, unlike regular surfaces such as planes, cylinders and conic surfaces. Free-form surfaces are known to the skilled person and widely used in engineering design disciplines. Typically non-uniform rational B-spline (NURBS) mathematics is used to describe the surface forms; however, there are other methods such as Gorden surfaces or Coons surfaces. The form of the free-form surfaces are characterized and defined not in terms of polynomial equations, but by their poles, degree, and number of patches (segments with spline curves). Free-form surfaces can also be defined as triangulated surfaces, where triangles are used to approximate the 3D surface. Triangulated surfaces are used in STL (Standard Triangulation Language) files that are known to a person skilled in CAD design. The free-form structures are structured such that they fit the surface of said object specifically, thereby giving the structures their free-form characteristics.

Typically, the bone plates are designed to comprise free-form structures, wherein said free-form structures are patient-specific, i.e. they are made to fit specifically in the anatomy of a certain (animal or human) body-part.

As used herein, the term "patient-specific features" relates to a feature such as a surface, which is designed, based on an individual patient's anatomy to include features that have a custom fit on a specific location in a specific patient. The use of the patient-specific features in the bone plates allows to ensure an improved or optimized accuracy of the positioning of the device and thus of the introduction of the anchoring device for each patient. Accordingly, the term "patient-specific device or surface" is used to refer to a custom-made device or surface specific to the individual patient's anatomy. In particular embodiments the bone plates may comprise at least one patient-specific element or surface that ensures a patient-specific fit on the anatomy of a patient. In particular embodiments, the patient-specific surface conforms to or is complementary with at least part of the patient's anatomy.

The step of manufacturing the bone plate envisaged in the context of the methods as disclosed herein typically involves methods that allow the generation of free-form objects according to a pre-determined design. In particular embodiments, the bone plate is manufactured at least partially by additive manufacturing.

Additive Manufacturing can be defined as a group of techniques used to fabricate a tangible model of an object typically using 3D computer aided design (CAD) data of the object. Currently, a multitude of Additive Manufacturing techniques is available, including stereolithography. Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3D object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The bone plate envisaged in the context of the present disclosure are thus typically made of material which is compatible with additive manufacturing and which is able to provide a sufficient stiffness to the free-form structure. Suitable materials include, but are not limited to polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESD7, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, CobaltChrome and Stainless Steel materials; Maranging Steel; Nickel Alloy; Titanium; the PA line of materials, PrimeCast and PrimePart materials and Alumide and CarbonMide from EOS GmbH.

A further aspect as disclosed herein relates to computer programs for carrying out the methods for generating the bone plates as disclosed herein. In particular embodiments, computer programs are provided, which, when run on a computer, generate the bone plates as disclosed herein. In particular embodiments the computer programs are adapted to perform the different steps of the methods as disclosed herein. In further embodiments, computer programs comprise software code adapted to perform the steps of the methods as disclosed herein. The data processing system or computer program particularly refer to computer aided design and manufacturing systems and programs such as CAD/CAM systems or programs. Said computer programs typically comprise tools for loading images of the object with the defect, tools for generating a 3D model of said bone defect based on the images, tools for generating a virtual element based on said 3D model and tools for designing the bone plate and optionally tools for instructing a manufacturing system to manufacture the bone plate according to the generated design.

As illustrated above, methods are disclosed for fixing a bone defect making use of the bone plates described herein. In particular embodiments such methods comprise providing a bone plate as described herein, such as by performing the methods as described herein above. The methods then comprise the step of placing the bone plate on the defective bone.

The provision of patient-specific or, more particularly, defect-specific bone plates can overcome certain problems associated with existing procedures for the repair of bone defects. Thus in particular embodiments, disclosed herein are bone plates and methods for making such bone plates for fixing a defect on an anatomical part. Thus, according to this aspect, orthopedic bone plates for fixing a defect in an anatomical part are provided, comprising (1) a positioning element for providing the first fixation of the bone plate onto the bone, (2) openings through which bone fixation elements are inserted into the bone to definitely anchor the bone plate to the target portions of the bone and (3) one or more patient-specific features ensuring the correct position of the bone plate onto the bone defect.

In addition, according to this aspect, methods for providing bone plates for fixing a defect on an anatomical part, more particularly a bone are provided, which methods comprise the steps of: generating a 2D or 3D model of the bone defect based on one or more medical images of the defective region of the anatomical part; designing based on said 2D or 3D model a model corresponding to the envisioned repair of said bone defect; generating a bone plate corresponding to the envisioned repair of said bone defect such that said bone plate comprises patient-specific features matching or corresponding to the surface of said model and the positions of the different positioning elements and openings for fixation elements; and making said bone plate based on said design.

In particular the bone plate is an orthopedic structure for use as an implant. The bone plate may comprise means allowing fixation to the patient's anatomical part in a region not affected by the defect. The bone plate provides structural strength during the healing process.

In these embodiments, the bone plates are typically made of biocompatible material. The orthopedic bone plates as described herein and the methods for making them disclosed herein have the advantage that the implants are made and ready for use prior to surgery, whereas current devices are generic and do not match with the patient's anatomy leading to more complex surgery. Also, the geometry of the orthopedic bone plate is determined in advance and based on the patient's specific situation, thereby providing a perfect fit, resulting in a better, faster and more accurate healing process. Also, the proper design of orthopedic bone plate is considered as one of the most important aspects for the success of the surgical intervention. Time spent before surgery evaluating the exact dimensions of the bone defect and then custom design of the implant has numerous advantages. Donor site pain and morbidity is eliminated or reduced with maximal use of synthetic replacement parts. Operative times can be reduced significantly, often cutting the length of an operation in half.

In yet a further aspect, methods for performing a surgical procedure on an anatomical part using the patient-specific bone plate are provided as described herein. The method comprises: a) drilling one or more holes into the bone or bone fragments according to a preoperative plan for the re-alignment of the bone fragments; b) inserting into at least one of said holes at least one of the positioning elements of a bone plate or bone plate assembly, thereby fitting at least part of the bone plate or bone plate assembly to the anatomical part; c) aligning the bone fragments and positioning the bone fragments into the position required for optimal healing; and; d) fixating the bone plate onto the bone fragment(s) by inserting fixating elements into the bone through fixation features (e.g. holes) on the bone plate, thereby securing the bone fragments in said required position.

The present method for performing a surgical procedure may further comprise the step of using the partially inserted bone plate of step b) as a hinge for aligning the bone defect in step c).

Typically, the present method for performing a surgical procedure further comprises the step of sterilizing the bone plate before fitting the bone plate to the anatomical part.

In certain embodiments, the present method for performing a surgical procedure further comprises the step of using a surgical guide to drill one or more holes into the bone fragments and/or to perform osteotomy on the anatomical part.

In yet a further aspect, kits are provided comprising tools for performing at least part of the surgical procedure. The kit typically comprises a patient specific bone plate as disclosed herein and a guide. More particularly for use in the placement of the bone plate envisaged herein, the guide may be a guide for drilling holes corresponding to the positioning elements of the bone plate as disclosed herein. In particular embodiments this implies that the guide is also patient-specific and allows the drilling of holes according to a pre-determined surgical plan for the placement of the bone plate. However, it may also be envisaged that the kit comprises the same or a different guide which serves as a cutting guide for performing the osteotomy. Indeed, the use of bone plates as envisaged herein typically involves performing osteotomy to allow repositioning of the bone-parts. In particular embodiments, the kit comprises a guide which is a drill guide and/or a cutting guide for performing the osteotomy. The kit may additionally or alternatively comprise external positioning elements and/or fixation elements for further fixating the bone plate into the correct position.

The present disclosure will be illustrated by the following non-limiting embodiments.

EXAMPLES

Figure 9:
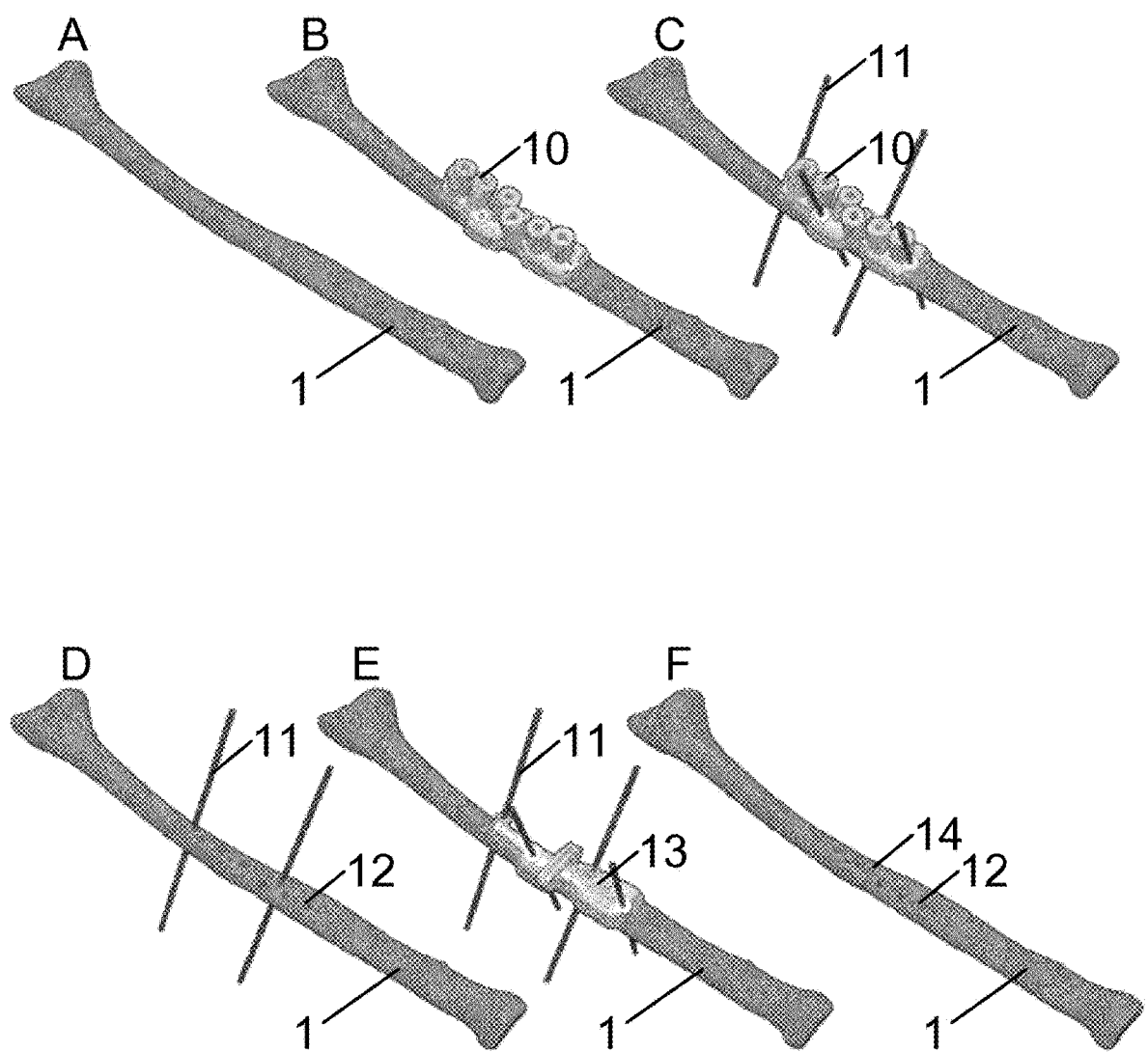
FIG. 9 illustrates an exemplified procedure for conducting a bone osteotomy.

FIG. 9 illustrates an exemplary embodiment where the different steps of a bone osteotomy are illustrated using guides and bone plates which are manufactured according to a pre-operative plan. A bone (1) is provided with a drill and/or cutting guide (10), which is used for drilling a number of holes in the bone (1) at predetermined positions. The drill guide comprises holes for introducing K-wires. After introduction of the K-wires (11) the drill guide (10) is removed (while the K-wires remain in place. A cutting guide (13) is put in place, using the K-wires for guidance and further K-wires are introduced and the bone osteotomy (14) is performed. The guide and K-wires can then be removed.

Figure 10:
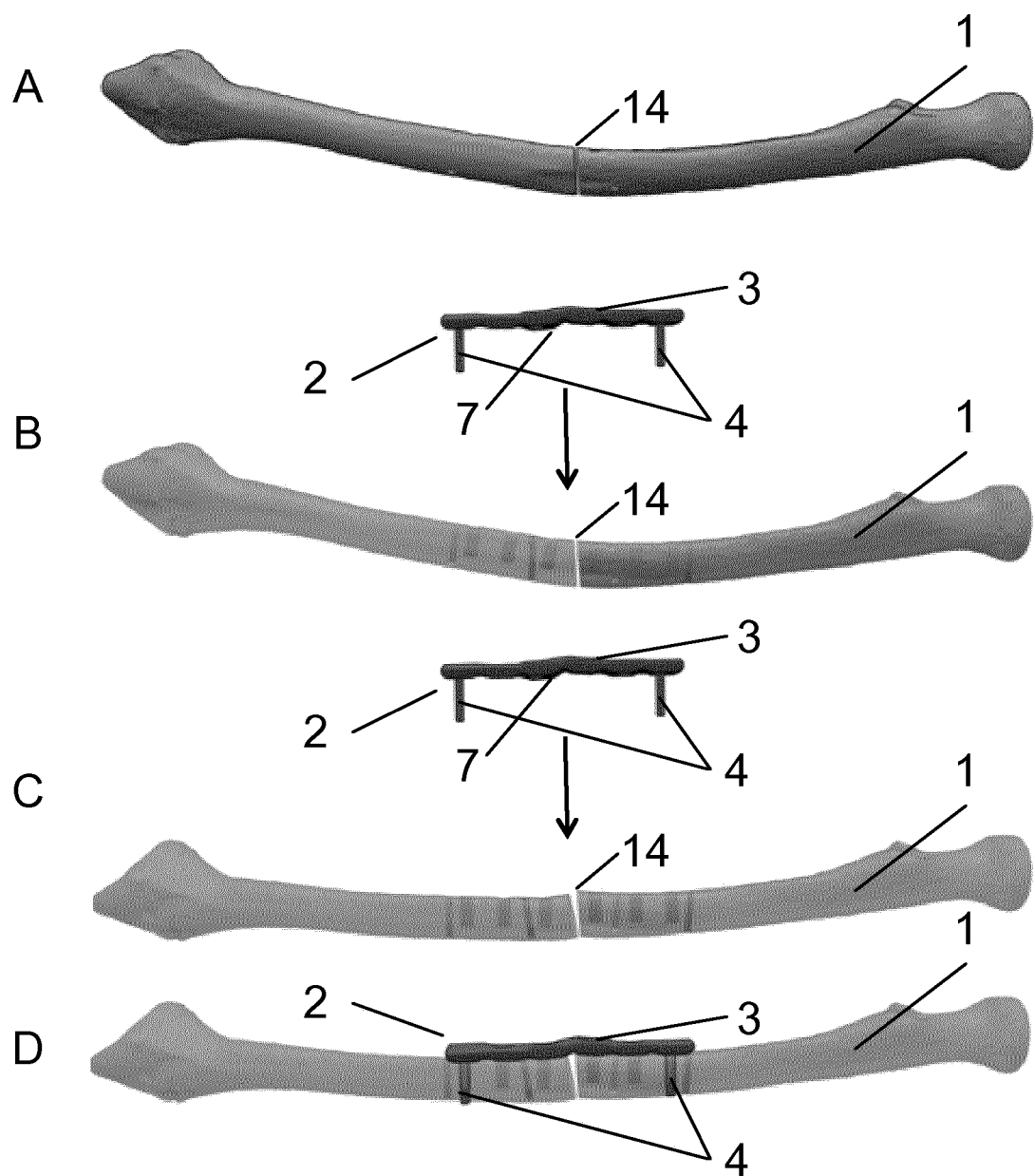
FIG. 10 illustrates the placement of a bone plate on a bone according to a particular embodiment.

FIG. 10 illustrates a specific embodiment where the different steps of positioning a bone plate are illustrated. A bone which has undergone a bone osteotomy (e.g. as illustrated in FIG. 1) is repositioned (from B to C) and a bone plate (2) having a supporting structure (3), a patient-specific part (7) and two pin-like positioning elements (4) is positioned onto the bone fragments, thereby positioning the bone fragments into a correct position for healing.

Figure 11:
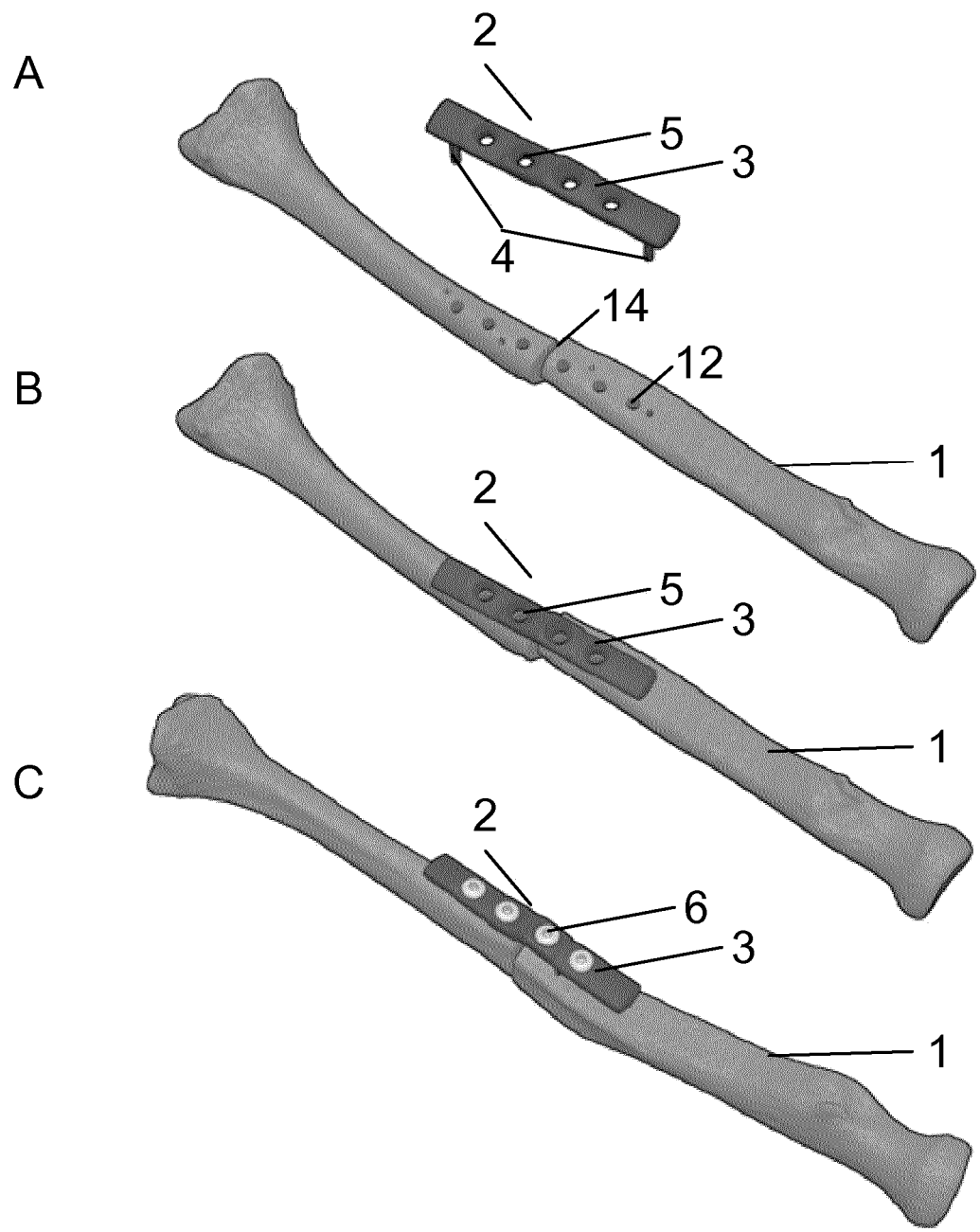
FIG. 11 illustrates the placement of a bone plate on a bone according to a particular embodiment.

FIG. 11 illustrates a specific embodiment where the different steps of positioning a bone plate are illustrated. A bone which has undergone a bone osteotomy or fracture is provided with a bone plate (2). Using the bone plate the correct position for healing is obtained and this correct healing position is fixated using fixation elements (6).

Figure 12:
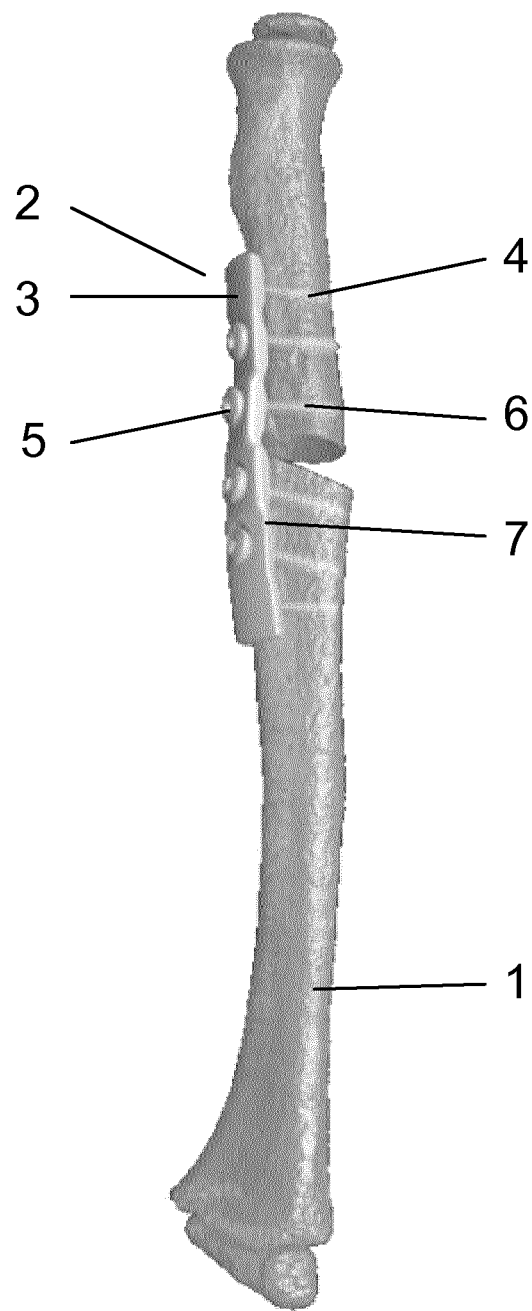
FIG. 12 illustrates an embodiment of a bone plate positioned on a bone.

FIG. 12 illustrates a specific embodiment of an orthopedic bone plate according to a particular embodiment. A fractured bone (1) has been repositioned into the correct healing position and this position is maintained using a bone plate (2) according to a particular embodiment. The bone plate (2) is provided with a supporting structure (3) which comprises positioning elements (4) for providing the first fixation of the bone plate onto the bone, fixation features (5) through which bone fixation elements (6) are inserted into the bone to definitely anchor the bone plate to the target portions of the bone and one or more patient-specific features (7) ensuring the correct position of the bone plate onto the bone defect. The orthopedic bone plate as illustrated in FIG. 4 can be used for the healing of large bone defects in long bones such as the femur, humerus or tibia. The implants are structurally stable and will not resorb or change their shape over time.

What is claimed is:

1. A patient-specific system for performing an osteotomy on a bone of a patient along a predetermined osteotomy cut plane, the system comprising:
   a first part comprising:
      at least one contact surface configured to conform to at least one portion of the bone such that when the at least one contact surface is positioned on the at least one portion of the bone, movement of the first part is substantially restricted with respect to the bone; and
      a plurality of guiding elements configured to guide placement of a plurality of reference pins by drilling in the bone such that two or more of the plurality of reference pins are inserted along the predetermined osteotomy cut plane for use to independently guide a cutting device along the predetermined osteotomy cut plane defined between the two or more of the plurality of reference pins, two or more of the plurality of guiding elements being aligned with the predetermined osteotomy cut plane;
   a second part, separate from the first part, the second part comprising:
      a plurality of apertures each with a shape corresponding to a reference pin, each of the plurality of apertures being configured to receive one of the plurality of reference pins and substantially restrict movement of the second part with respect to the bone when the plurality of reference pins are received; and
      at least one functional element for drilling a hole in the bone; and
   an osteosynthesis plate comprising a first aperture configured to align with the hole in the bone when positioned on the bone.

2. The system of claim 1, wherein the plurality of guiding elements comprises a drill guide.

3. The system of claim 1, wherein the second part further comprises a first contact surface configured to conform to at least a second portion of the bone when the plurality of reference pins are received, wherein the first contact surface is configured such that contact between the first contact surface and the bone alone is insufficient to substantially restrict movement of the second part with respect to the bone.

4. The system of claim 1, wherein the at least one functional element comprises a drill guide.

5. The system of claim 1, wherein the osteosynthesis plate further comprises a second aperture, wherein each of the first aperture and the second aperture is configured to receive an implant fixation element, wherein the at least one functional element comprises a plurality of drill guides, and wherein the first aperture and the second aperture are each configured to align with a position on the bone corresponding to a position on the bone of one of the plurality of drill guides when the plurality of reference pins are received by the plurality of apertures.

6. The system of claim 5, wherein the first aperture and the second aperture are separated by a first distance, and wherein a first drill guide corresponding to the first aperture and a second drill guide corresponding to the second aperture are separated by a second distance, wherein the first distance is different than the second distance.

7. The system of claim 6, wherein the first aperture is associated with a first bone position that is on a first side of the osteotomy cut plane and wherein the second aperture is associated with a second bone position that is on a second side of the osteotomy cut plane, the first side being opposite the second side.

8. The system of claim 5, wherein the implant fixation element comprises a screw.

9. The system of claim 1, wherein the at least one functional element comprises a cut-guiding surface.

10. The system of claim 1, wherein the at least one functional element comprises one or more radiopaque elements.

11. The system of claim 1, wherein the first part comprises tapered edges.

12. The system of claim 1, wherein the first part conforms to a profile between 1 to 3 mm.

13. The system of claim 1, wherein the second part does not extend beyond the plurality of apertures and the at least one functional element by more than a threshold amount, the threshold amount being 3 mm.

14. The system of claim 1, wherein the first part comprises flexible portions for removing the first part from the bone with the reference pins placed in the plurality of guiding elements.

15. A method for performing an osteotomy on a bone of a patient along a predetermined osteotomy cut plane, the method comprising:
   placing a first part of a two-part osteotomy guide within a surgical site of the bone of the patient, the first part comprising:
      at least one contact surface configured to conform to at least one portion of the bone such that when the at least one contact surface is positioned on the at least one portion of the bone, movement of the first part is substantially restricted with respect to the bone; and
      a plurality of guiding elements configured to guide placement of a plurality of reference pins by drilling in the bone such that two or more of the plurality of reference pins are inserted on the predetermined osteotomy cut plane for use to independently guide a cutting device along the predetermined osteotomy cut plane defined between the two or more of the plurality of reference pins, two or more of the plurality of guiding elements being aligned with the predetermined osteotomy cut plane;
positioning the first part on the bone by aligning the at least one contact surface with the at least one portion of the bone to secure the first part to the bone;
guiding placement of the plurality of reference pins into the bone based on the plurality of guiding elements;
removing the first part from the bone;
positioning a second part of the two-part osteotomy guide on the bone by receiving the reference pins in a plurality of apertures of the second part, the second part comprising:
 the plurality of apertures each with a shape corresponding to a reference pin, each of the plurality of apertures being configured to receive one of the plurality of reference pins and substantially restrict movement of the second part with respect to the bone when the plurality of reference pins are received; and
 at least one functional element for guiding a procedure on the bone;
drilling at least one hole into the bone through the at least one functional element;
removing the second part from the bone;
performing an osteotomy cut to the bone along the predetermined osteotomy cut plane with reference to the plurality of reference pins; and
securing an osteosynthesis plate comprising a first aperture configured to align with the at least one drilled hole in the bone when positioned on the bone to the bone using the at least one drilled hole.

16. The method of claim 15, wherein positioning the first part on the bone comprises positioning at least part of the first part between a soft tissue of the patient and the bone.

17. The method of claim 15, further comprising changing a position of at least a portion of the bone after performing the osteotomy cut and before securing the osteosynthesis plate to the bone.

18. The method of claim 15, wherein removing the first part from the bone comprises flexing a portion of the first part to remove the first part from the bone while the reference pins are inserted through the plurality of guiding elements.

19. The method of claim 15, further comprising performing a second osteotomy cut to the bone.

* * * * *